(12) United States Patent
Balanov et al.

(10) Patent No.: US 7,678,799 B2
(45) Date of Patent: Mar. 16, 2010

(54) CRYSTALLINE ZIPRASIDONE HCL AND PROCESSES FOR PREPARATION THEREOF

(75) Inventors: Anna Balanov, Rehovot (IL); Judith Aronhime, Rehovot (IL); Boaz Gome, Rishon-Lezion (IL); Tamas Koltai, Natanja (IL); Natalia Shenkar, Petach Tiqva (IL); Marioara Mendelovici, Rehovot (IL); Ehud Amir, Ramat-Aviv (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 1300 days.

(21) Appl. No.: 10/860,864

(22) Filed: Jun. 3, 2004

(65) Prior Publication Data

US 2005/0059680 A1 Mar. 17, 2005

Related U.S. Application Data

(60) Provisional application No. 60/475,806, filed on Jun. 3, 2003, provisional application No. 60/487,913, filed on Jul. 16, 2003, provisional application No. 60/494,970, filed on Aug. 13, 2003, provisional application No. 60/528,346, filed on Dec. 9, 2003, provisional application No. 60/571,997, filed on May 17, 2004.

(51) Int. Cl.
*C07D 417/14* (2006.01)

(52) U.S. Cl. ........................ 514/254; 544/368
(58) Field of Classification Search ............ 514/254; 544/254
See application file for complete search history.

(56) References Cited

U.S. PATENT DOCUMENTS

| | | | | |
|---|---|---|---|---|
| 4,831,031 A | * | 5/1989 | Lowe et al. | 514/254.02 |
| 5,206,366 A | | 4/1993 | Bowles | |
| 5,312,925 A | * | 5/1994 | Allen et al. | 544/368 |
| 5,338,846 A | | 8/1994 | Busch et al. | |
| 5,359,068 A | | 10/1994 | Urban | |
| 6,110,918 A | | 8/2000 | Busch et al. | |
| 6,150,366 A | | 11/2000 | Arenson et al. | |
| 2002/0016498 A1 | | 2/2002 | Am Ende et al. | |
| 2004/0048876 A1 | | 3/2004 | Busch et al. | |
| 2005/0143396 A1 | | 6/2005 | Parthasaradhi et al. | |

FOREIGN PATENT DOCUMENTS

| | | |
|---|---|---|
| EP | 0 584 903 A1 | 3/1994 |
| EP | 0 586 181 A2 | 3/1994 |
| EP | 0586191 A1 | 3/1994 |
| EP | 0 965 343 A2 | 12/1999 |
| EP | 0 965 343 B1 | 12/1999 |
| EP | 1157726 A1 | 11/2001 |
| WO | WO 97/42191 | 11/1997 |
| WO | WO-03/070246 | 8/2003 |
| WO | WO 2004/050655 | 6/2004 |
| WO | WO 2004/054621 | 7/2004 |
| WO | WO 2004/070246 | 8/2004 |
| WO | WO 2004/089948 | 10/2004 |

OTHER PUBLICATIONS

US 5,245,765, (withdrawn).
*J. Phys. D: Appl. Phys.* 26 (Aug. 14, 1993) B181-B187.
EL Parrott, in *Pharmaceutical Techology: Fundamental Pharmaceutics*, Burgess, Minneapolis, Minn., 1970, pp. 1-36.
EL Parrott, *Pharm. Manuf.*, 2, 30-37 (1985).
SL Lowell and JE Shields, *Powder Surface Area and Porosity*, Chapman and Hall New York, 1984.
S. Brunauer, PH Emmett and E Teller, *J.Am.Chem. Soc.*, 6, 309 (1938).
Pages of Laboratory Notebook, pp. 189, 086, 087, 122, 164, 166-169. Jul. 29, 2009.

* cited by examiner

*Primary Examiner*—James O. Wilson
*Assistant Examiner*—Paul V. Ward
(74) *Attorney, Agent, or Firm*—Kenyon & Kenyon LLP

(57) ABSTRACT

Provided is crystalline ziprasidone HCl and processes for preparation thereof.

26 Claims, 15 Drawing Sheets

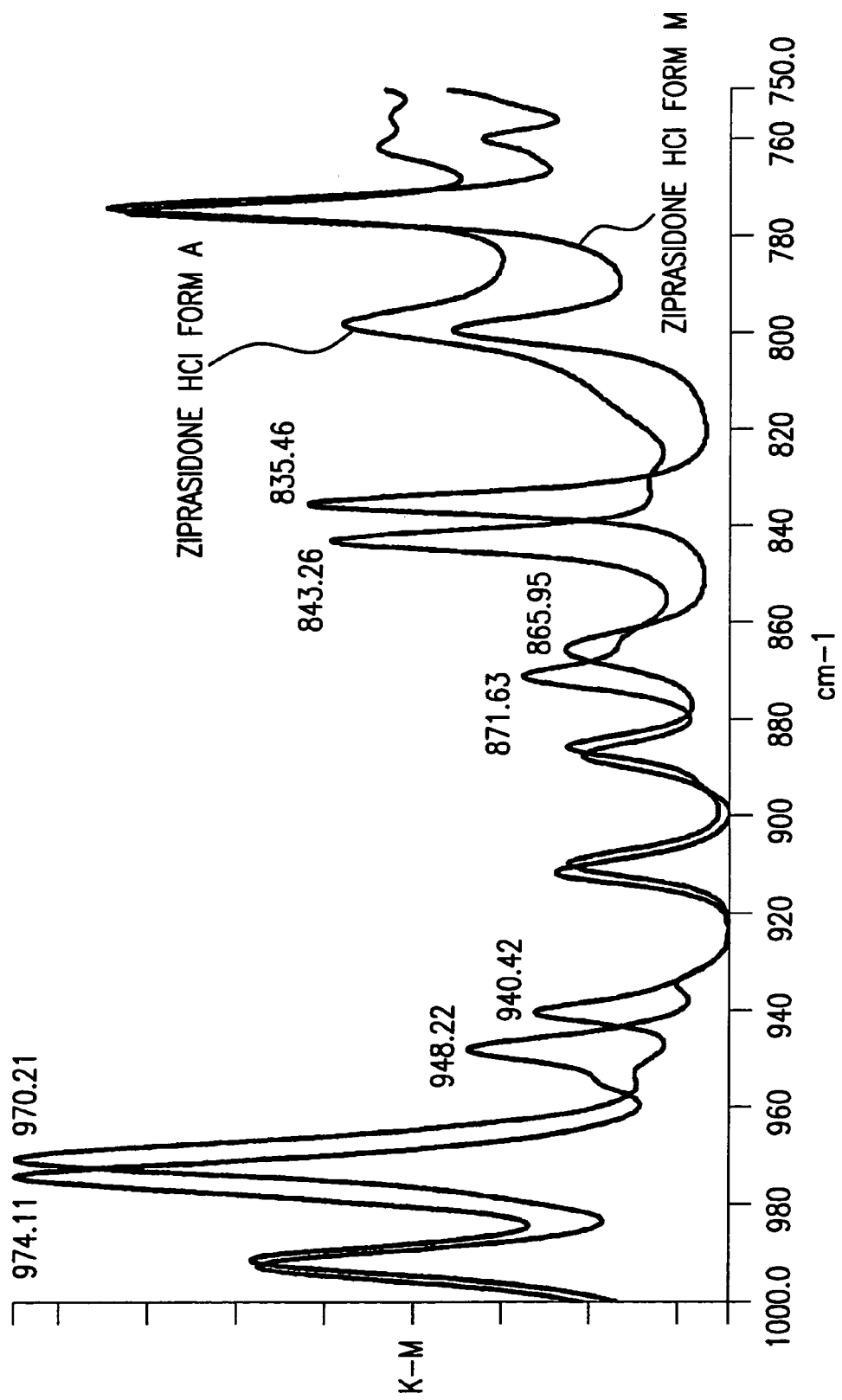

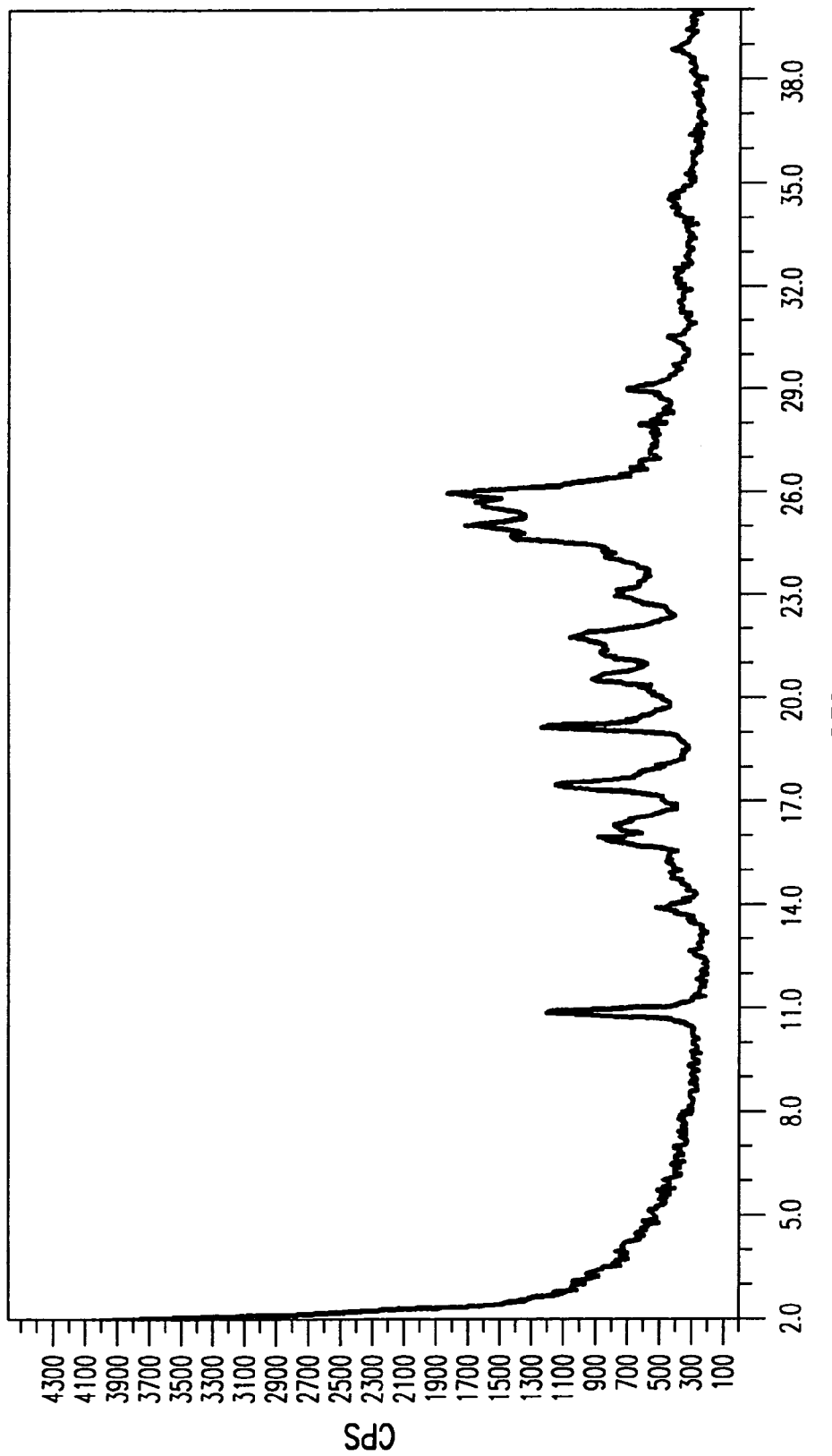

CRYSTALLINE ZIPRASIDONE HCL AND PROCESSES FOR PREPARATION THEREOF

CROSS REFERENCE TO RELATED APPLICATIONS

This application claims the benefit of U.S. provisional application Ser. No. 60/475,806, filed Jun. 3, 2003; U.S. provisional application Ser. No. 60/487,913, filed Jul. 16, 2003; U.S. provisional application Ser. No. 60/494,970, filed Aug. 13, 2003; U.S. provisional application Ser. No. 60/528,346, filed Dec. 9, 2003, and U.S. provisional application Ser. No. 60/571,997; filed, May 17, 2004, the contents of all of which are incorporated herein.

FIELD OF THE INVENTION

The present invention relates to the solid state chemistry of ziprasidone HCl.

BACKGROUND OF THE INVENTION

Ziprasidone is an antipsychotic agent that is chemically unrelated to phenothiazine or butyrophenone antipsychotic agents. Ziprasidone has the following structure:

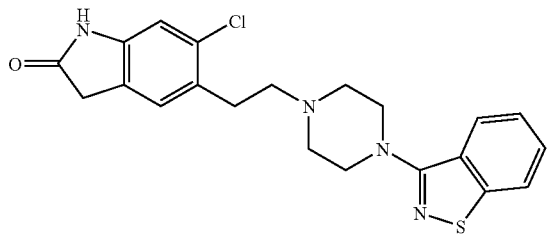

The preparation of ziprasidone base is disclosed in U.S. Pat. No. 4,831,031 (example 16). Preparation of ziprasidone base is also disclosed in U.S. Pat. No. 5,312,925. A process for preparation of ziprasidone HCl monohydrate having a mean particle size equal to or less than about 85 microns is also disclosed in U.S. Pat. No. 6,150,366 and EP 0 965 343 A2.

Ziprasidone has been marketed under the name GEODON as an oral capsule and as an injectable drug. GEODON capsules contain the monohydrate hydrochloride salt of ziprasidone, and come in 20, 40, 60 and 80 mg dosage forms. GEODON for injection contains a lyophilized form of ziprasidone mesylate trihydrate, and contains 20 mg base equivalent of ziprasidone. The mesylate salts of ziprasidone, including monohydrate and trihydrate, are disclosed in U.S. Pat. Nos. 6,110,918 and 5,245,765.

The present invention relates to the solid state physical properties of ziprasidone HCl. These properties can be influenced by controlling the conditions under which ziprasidone HCl is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

Ziprasidone HCl has very low solubility in water (0.08 mg/ml). Increase in specific surface area (SSA) of low aqueous solubility materials may improve therapeutic activity (J. Phys. D: Appl. Phys. 26 (14 Aug. 1993) B181-B187). The surface area of a solid material provides information about the void spaces on the surfaces of individual particles or aggregates of particles (E L Parrott, in Pharmaceutical Technology: Fundamental Pharmaceutics, Burgess, Minneapolis, Minn., 1970, pp 1-36). Factors such as chemical activity, adsorption, dissolution, and bioavailability of the drug may depend on the surface of the solid (E L Parrott, in Pharmaceutical Technology: Fundamental Pharmaceutics, Burgess, Minneapolis, Minn., 1970, pp 1-36, E L Parrott, Pharm. Manuf., 2, 30-37 (1985)). The adsorption of inert gases onto solid materials represents the most widely used method for the determination of SSA, although other methods are available (S L Lowell and J E Shields, Powder Surface Area and Porosity, Chapman and Hall New York, 1984). The BET method (S. Brunauer, P H Emmett and E Teller, J. Am. Chem. Soc., 60, 309 (1938)) is generally used for gas adsorption surface area measurement.

These practical physical characteristics are influenced by the conformation and orientation of molecules in the unit cell, which defines a particular polymorphic form of a substance. These conformational and orientational factors in turn result in particular intramolecular interactions and intermolecular interactions with adjacent molecules that influence the macroscopic properties of the bulk compound. A particular polymorphic form may give rise to distinct spectroscopic properties that may be detectable by powder X-ray diffraction, solid state $^{13}$C NMR spectrometry and infrared spectrometry. The polymorphic form may also give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others.

Ziprasidone HCl hemihydrate is disclosed in U.S. Pat. No. 4,831,031, Example 16 (column 13, line 13). A crystalline form of ziprasidone HCl (herein designated Form M) is disclosed in U.S. Pat. No. 5,312,925 and EP 0 586 181 A1. Form M is characterized by XRD, IR and water content. It is reported that the water content of Form M ranges from 3.8 to 4.5% by weight, and that it is a monohydrate. Ziprasidone HCl Form M is prepared from ziprasidone base anhydrous.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. There is a need in the art for additional polymorphic forms of ziprasidone HCl.

SUMMARY OF THE INVENTION

In one aspect, the present invention provides for crystalline ziprasidone HCl, denominated Form A, characterized by data selected from the group consisting of a powder XRD pattern with peaks at 10.9, 17.4 and 19.1±0.2 degrees 2 theta and an FTIR spectrum with peaks at about 3400, 3344, 3172, 2949, 970, 940, 872 and 843 cm$^{-1}$.

In another aspect, the present invention also provides crystalline ziprasidone HCl form A, which consists of less than about 5% Form M.

In another aspect, the present invention also provides crystalline ziprasidone HCl form A, which does not transform to Form M by more than 5% upon heating.

In another aspect, the present invention also provides crystalline ziprasidone HCl form A, which does not transform to Form M by more than 5% upon storage at 0% humidity for 20 days or more.

In another aspect, the present invention also provides crystalline ziprasidone HCl form A, which does not transform to Form M by more than 5% upon storage at a temperature of between about 25° and 55° C. for at least 3 months.

In another aspect, the present invention also provides crystalline ziprasidone HCl form A, which has a specific surface area higher than about 4 m$^2$/g.

In another aspect, the present invention also provides crystalline ziprasidone HCl form A, which has high crystallinity.

In another aspect, the present invention provides a process for preparing crystalline ziprasidone HCl form A comprising:
 a) providing a slurry of ziprasidone base, aqueous HCl and a solvent selected from the group consisting of toluene, monochlorobenzene, methanol, ethanol, diethyl-carbonate, water, isopropyl alcohol and mixtures thereof;
 b) maintaining the slurry to obtain crystalline ziprasidone HCl; and
 c) recovering the crystalline ziprasidone HCl.

In another aspect, the present invention also provides a process for preparing crystalline ziprasidone HCl form A comprising:
 a) dissolving, while stirring, ziprasidone base in a mixture of C$_{1-4}$ alcohol and an organic acid;
 b) adding water and aqueous HCl to the solution;
 c) recovering the crystalline ziprasidone HCl.

In another aspect, the present invention also provides a process for preparing crystalline ziprasidone HCl form A, comprising:
 a) providing a slurry of ziprasidone HCl characterized by a powder XRD pattern of 7.4, 13.0, 20.7, 23.4, 25.9±0.2 degrees 2 theta in THF or ethanol;
 b) maintaining the slurry to obtain the crystalline ziprasidone HCl; and
 c) recovering the crystalline ziprasidone HCl.

In another aspect, the present invention provides a process for preparing crystalline ziprasidone HCl form A comprising exposing ziprasidone HCl characterized by a powder XRD pattern of 7.4, 13.0, 20.7, 23.4, 25.9±0.2 degrees 2 theta to a relative humidity of about 20% to about 60%;

In another aspect, the present invention provides a process for preparing crystalline ziprasidone HCl form A substantially free of ziprasidone HCl Form M comprising:
 a) preparing a slurry of ziprasidone HCl in water, optionally in the presence of an organic solvent, at a temperature of about 0° C. to about 40° C.;
 b) maintaining the slurry to obtain the crystalline ziprasidone HCl; and
 c) recovering the ziprasidone HCl.
 wherein the slurry is prepared by combining aqueous HCl in less than about 30 minutes with ziprasidone base in water.

In another aspect, the present invention provides a process for preparing ziprasidone HCl Form M comprising heating a slurry of the crystalline ziprasidone HCl Form A in ethanol.

In another aspect, the present invention provides a solid crystalline ziprasidone HCl having a water content of about 4.6% to about 6.6% by weight.

In another aspect, the present invention provides a process for preparing a solid crystalline ziprasidone HCl having a water content of about 4.6% to about 6.6% by weight comprising maintaining a slurry of ziprasidone HCl Form E in THF at a temperature below about 40° C.

In another aspect, the present invention provides a process for preparing a solid crystalline ziprasidone HCl having a water content of about 4.6% to about 6.6% by weight comprising maintaining a slurry of ziprasidone HCl Form E in THF at a temperature below about 40° C., drying solid obtained from the slurry at elevated temperature, contacting the solid with humid air to obtain the desired water content.

In another aspect, the present invention provides a solid crystalline ziprasidone HCl having a water content of about 4.6% to about 6.6% by weight which does not transform to Form M by more than 5% upon storage at 0% humidity for 20 days or more.

In another aspect, the present invention provides a solid crystalline ziprasidone HCl having a water content of about 4.6% to about 6.6% by weight which does not transform to Form M by more than 5% upon storage at a temperature of between about 25° and 55° C. for at least 3 months In another aspect, the present invention provides for solid crystalline ziprasidone HCl having specific surface area higher than about 4 m$^2$/g.

Also provided are pharmaceutical compositions and a method of treating a patient suffering from schizophrenia.

FIGURES

FIG. 6 is an IR spectra of crystalline ziprasidone HCl Forms A and M.

DETAILED DESCRIPTION OF THE INVENTION

As used herein, the term slurry refers to a heterogeneous mixture.

As used herein, the term reduced pressure refers to a pressure below about 1 atm, more preferably below about 100 mmHg.

Figure 1:
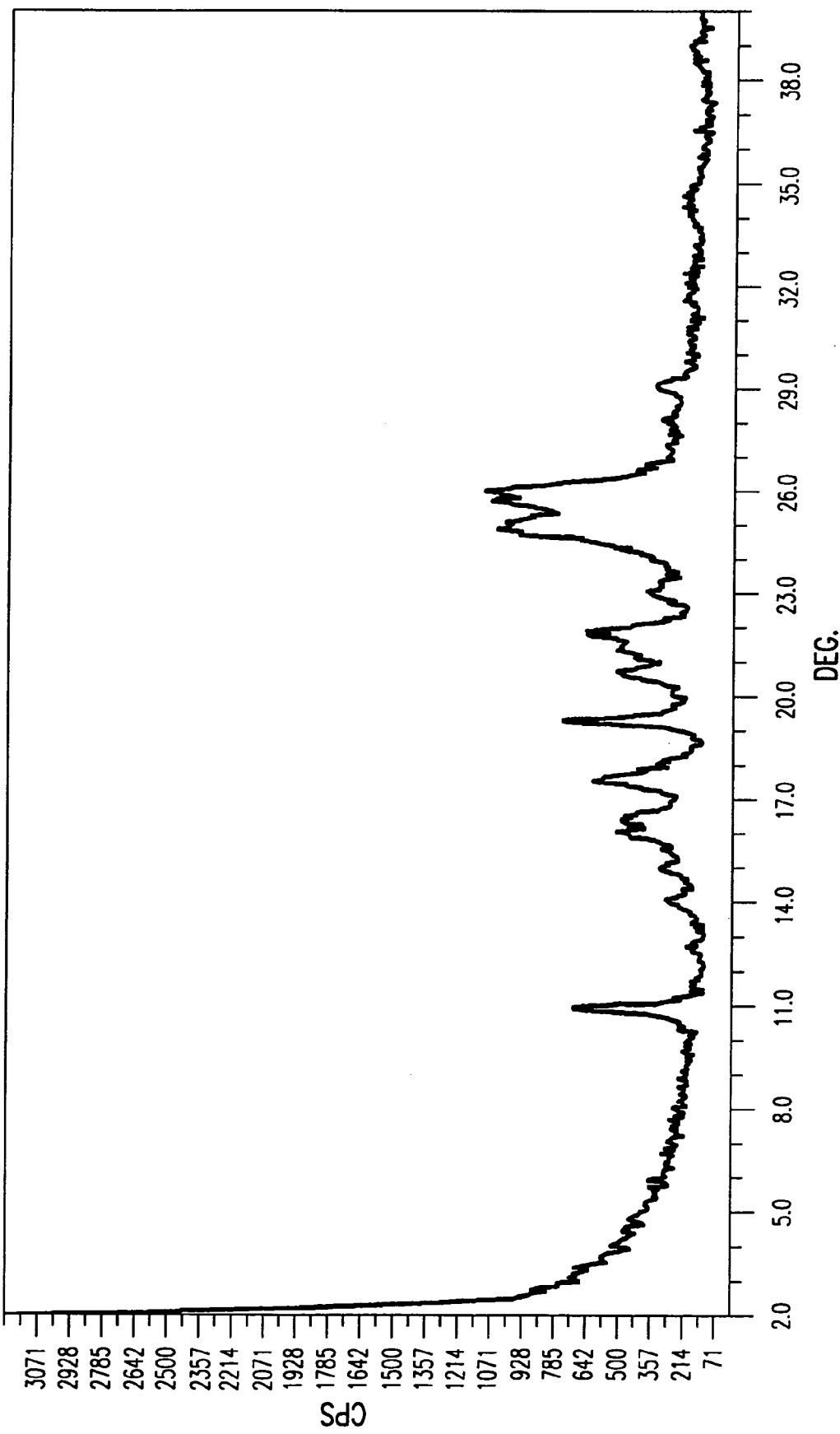
FIG. 1 is an X-Ray powder diffractogram of crystalline ziprasidone HCl Form A
Figure 2:
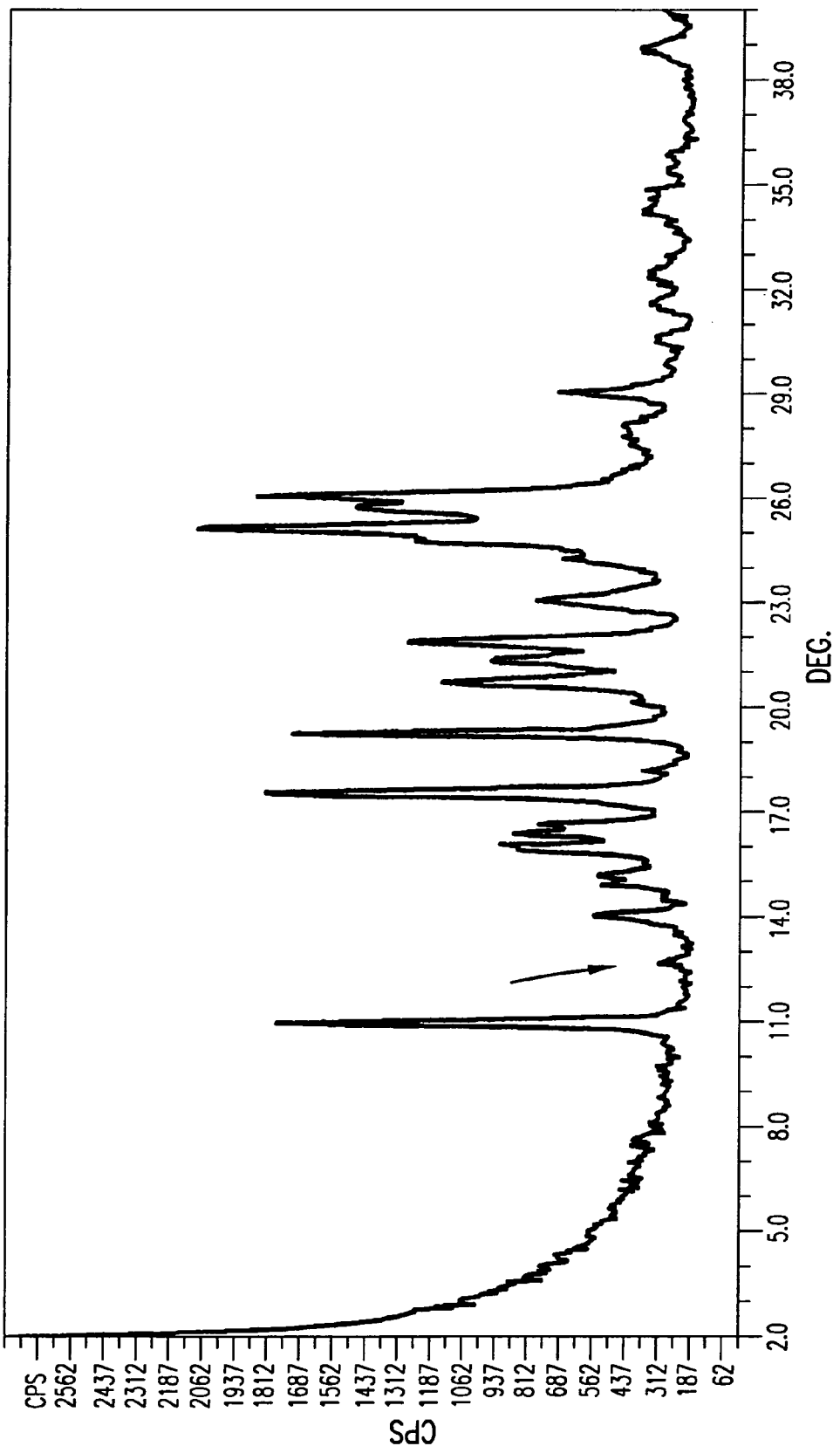
FIG. 2 is an X-Ray powder diffractogram of high crystallinity ziprasidone HCl Form A, containing about 5% Form M.
Figure 3:
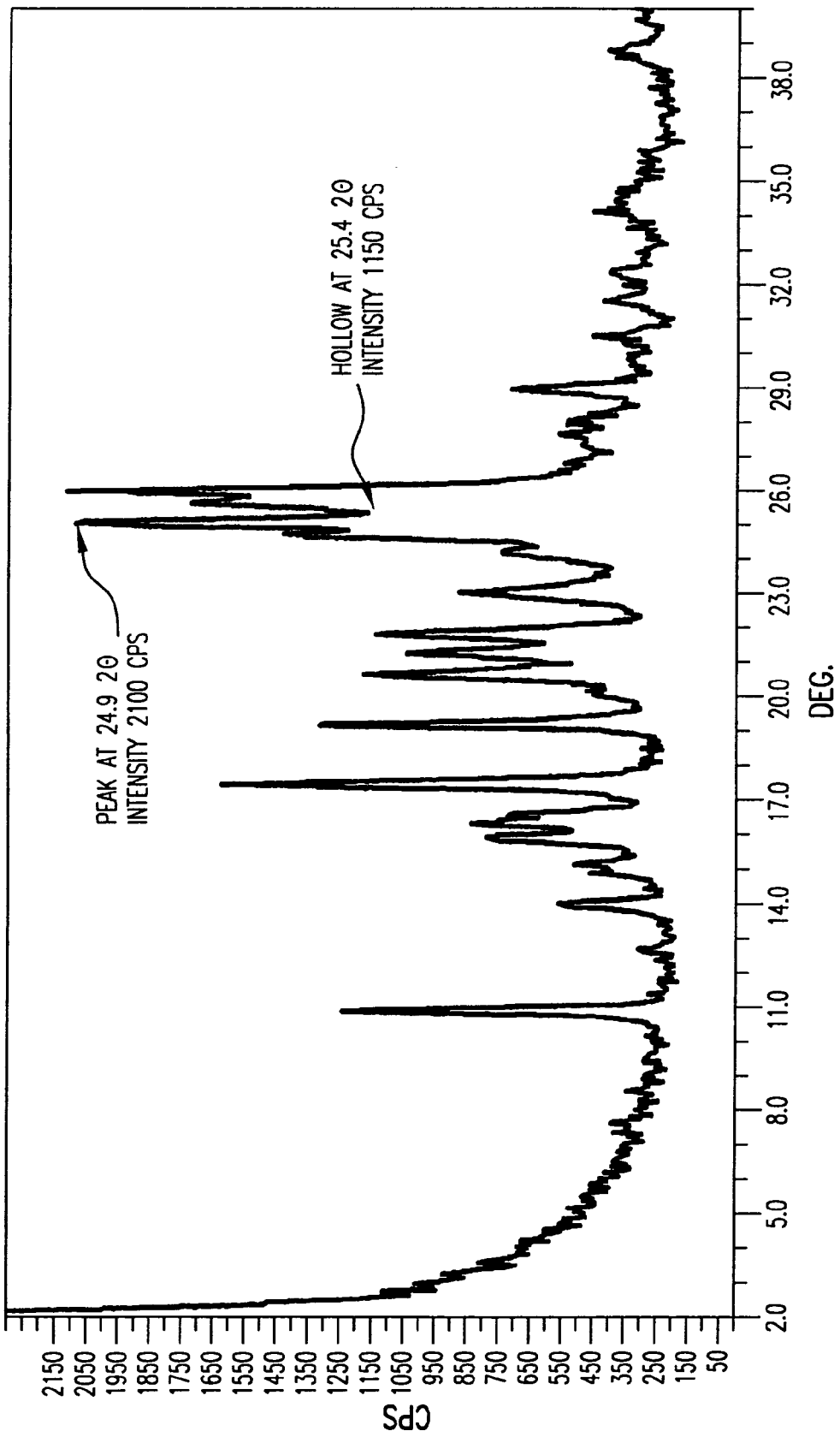
FIG. 3 is an X-Ray powder diffractogram of high crystallinity ziprasidone HCl Form A.
Figure 4:
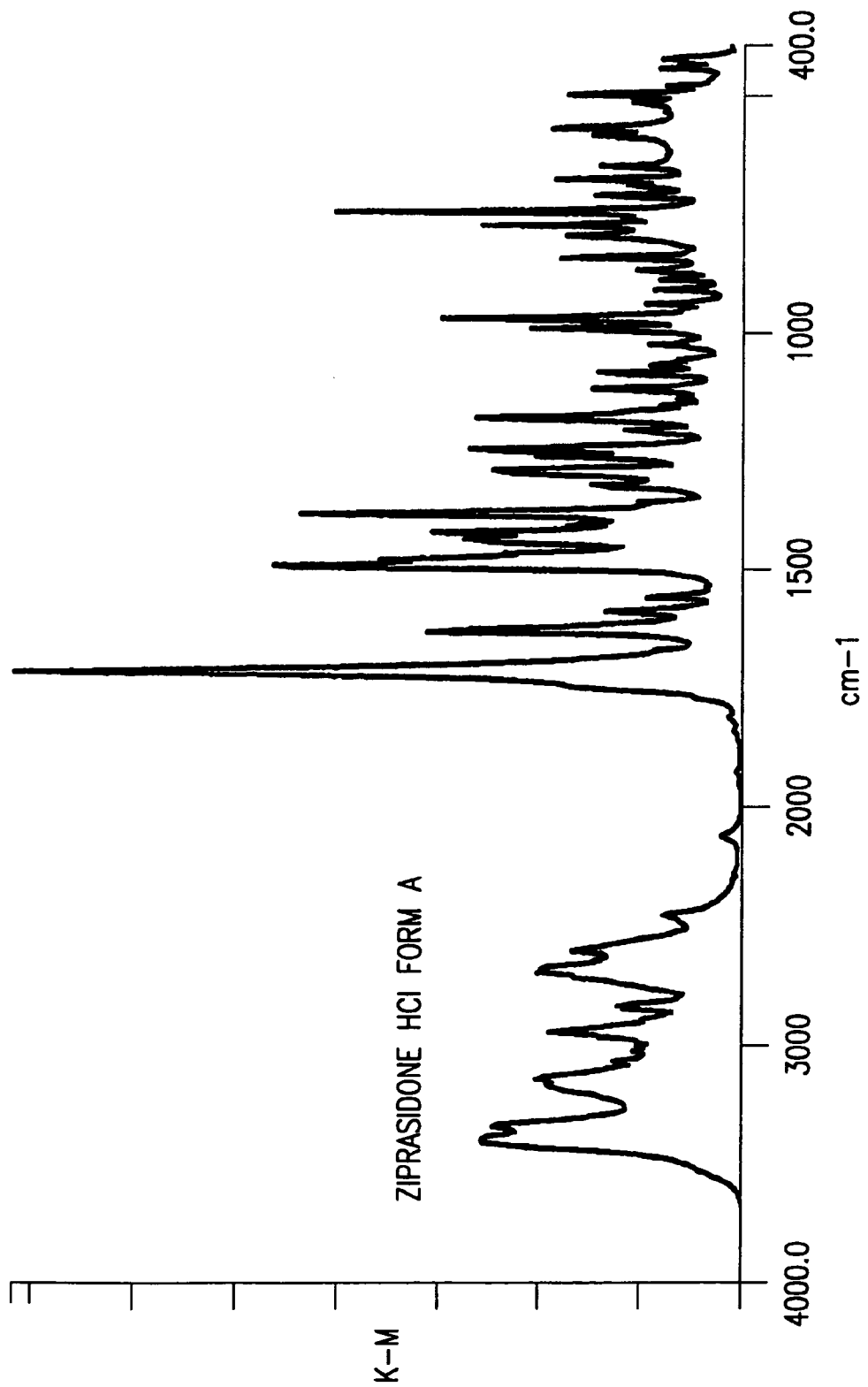
FIG. 4 is an IR spectra of crystalline ziprasidone HCl Form A.
Figure 5:
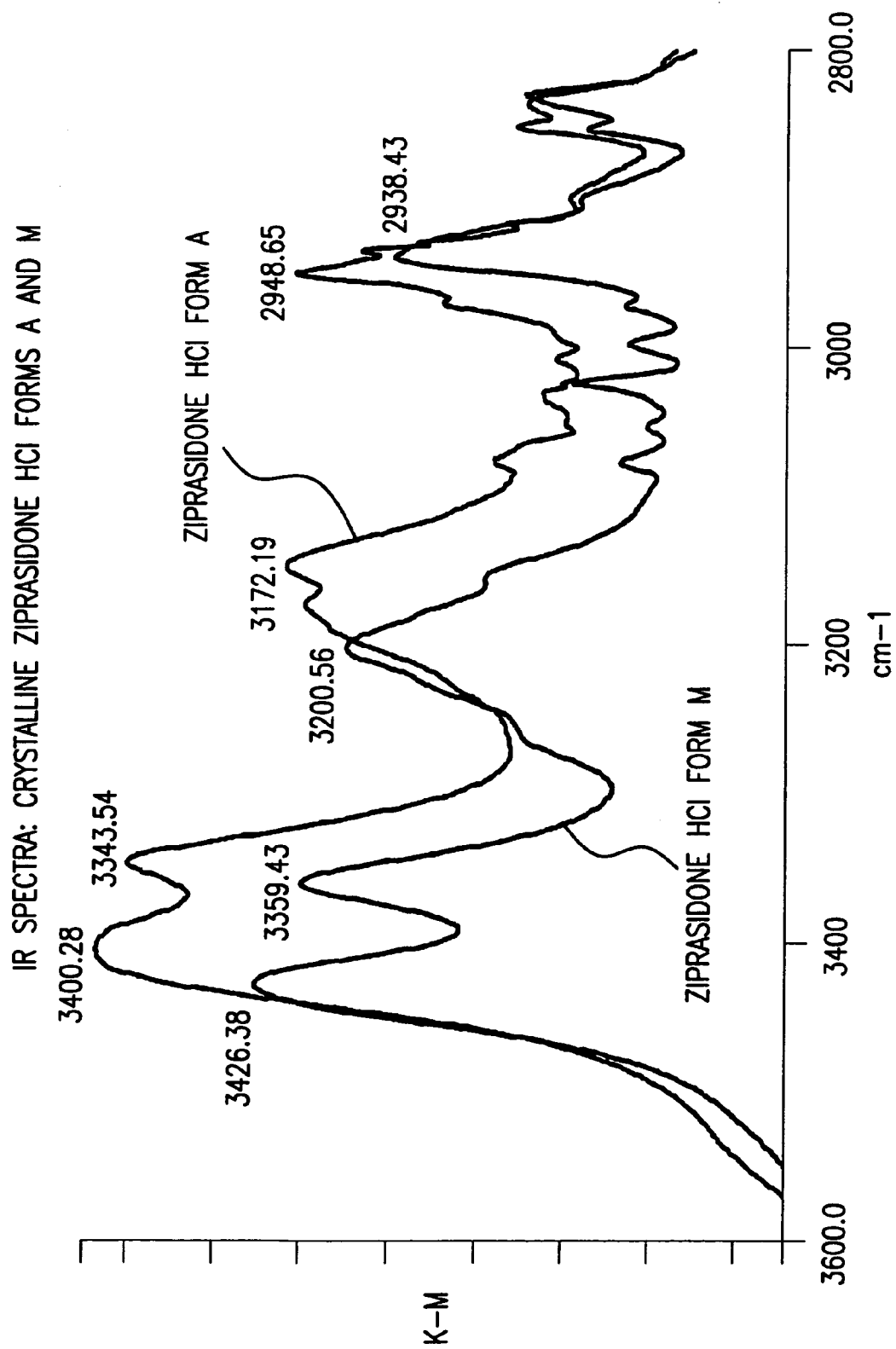
FIG. 5 is an IR spectra of crystalline ziprasidone HCl Forms A and M.

In one aspect, the present invention provides for crystalline ziprasidone HCl, denominated Form A, characterized by data selected from the group consisting of an X-Ray diffraction pattern having peaks at about 10.9, 17.4 and 19.1±0.2 degrees 2 theta, substantially as depicted in FIG. 1, and an FTIR spectrum with characteristic absorption bands at about 3400, 3344, 3172, 2949, 970, 940, 872 and 843 cm$^{-1}$, substantially as depicted in FIGS. 4 and 5. Crystalline ziprasidone HCl Form A of the present invention may be further characterized by XRD peaks at 25.0 and 26.0±0.2 degrees two-theta, and may be further characterized by XRD peaks at 13.9, 20.6, 21.3, 21.8 and 23.0±0.2 degrees two-theta. The crystalline ziprasidone HCl Form A provided in the present invention has a water content of about 0.5% to about 6.6% by weight, and may have high crystallinity, substantially as depicted in FIGS. 2 and 3.

The FTIR spectra of Forms A and M are similar, however differences can be seen in the ranges of 3600-2800 and 1000-750 cm$^{-1}$, substantially as depicted in FIGS. 4 and 5.

Ziprasidone HCl Form A may exist with crystallinity level. Crystalline ziprasidone HCl Form A and high crystallinity ziprasidone HCl Form A have the same characteristic peaks in XRD. However the peak width at half height for high crystalline ziprasidone is smaller than for crystalline ziprasidone HCl Form A; the peaks for high crystalline ziprasidone are sharper and well defined, while in the crystalline ziprasidone the peaks are wider and less resolved.

The peak width at half height for the peak at 10.9° 2Θ is 0.21° for high crystalline ziprasidone, and 0.30 for crystalline ziprasidone. For the peak at 17.4° 2Θ, 0.25° for high crystalline ziprasidone and 0.48 for crystalline ziprasidone. For the peak at 19.1° 2Θ, 0.20° for high crystalline ziprasidone and 0.30 for crystalline ziprasidone. For the peak at 23.0° 2Θ, 0.37° for high crystalline ziprasidone and 0.54° for crystalline ziprasidone. Preferably, the crystalline form has peaks with a higher than about the average width as illustrated (average of the two widths provided), more preferably higher than about 75% of the range of the two widths provided.

Some Peak width at half height for Crystalline ziprasidone HCl Form A and high crystallinity ziprasidone HCl Form A

| Peaks ± 0.2 degrees 2 theta | Peak width at half height for Crystalline ziprasidone HCl Form A (degrees 2 theta) | Peak width at half height for high crystallinity ziprasidone HCl Form A (degrees 2 theta) |
| --- | --- | --- |
| 10.9 | 0.30 | 0.21 |
| 17.4 | 0.48 | 0.25 |
| 19.1 | 0.30 | 0.20 |
| 23.0 | 0.54 | 0.37 |

The crystalline ziprasidone HCl Form A of the present invention may be substantially free from other crystalline forms, i.e. no more than about 5% of other crystalline forms, preferably Form M. A suitable technique for monitoring the crystalline content is X-Ray powder diffraction. In addition, no more than 5% of Form A transforms into Form M during heating and also during exposure to 0% relative humidity.

Figure 7A:
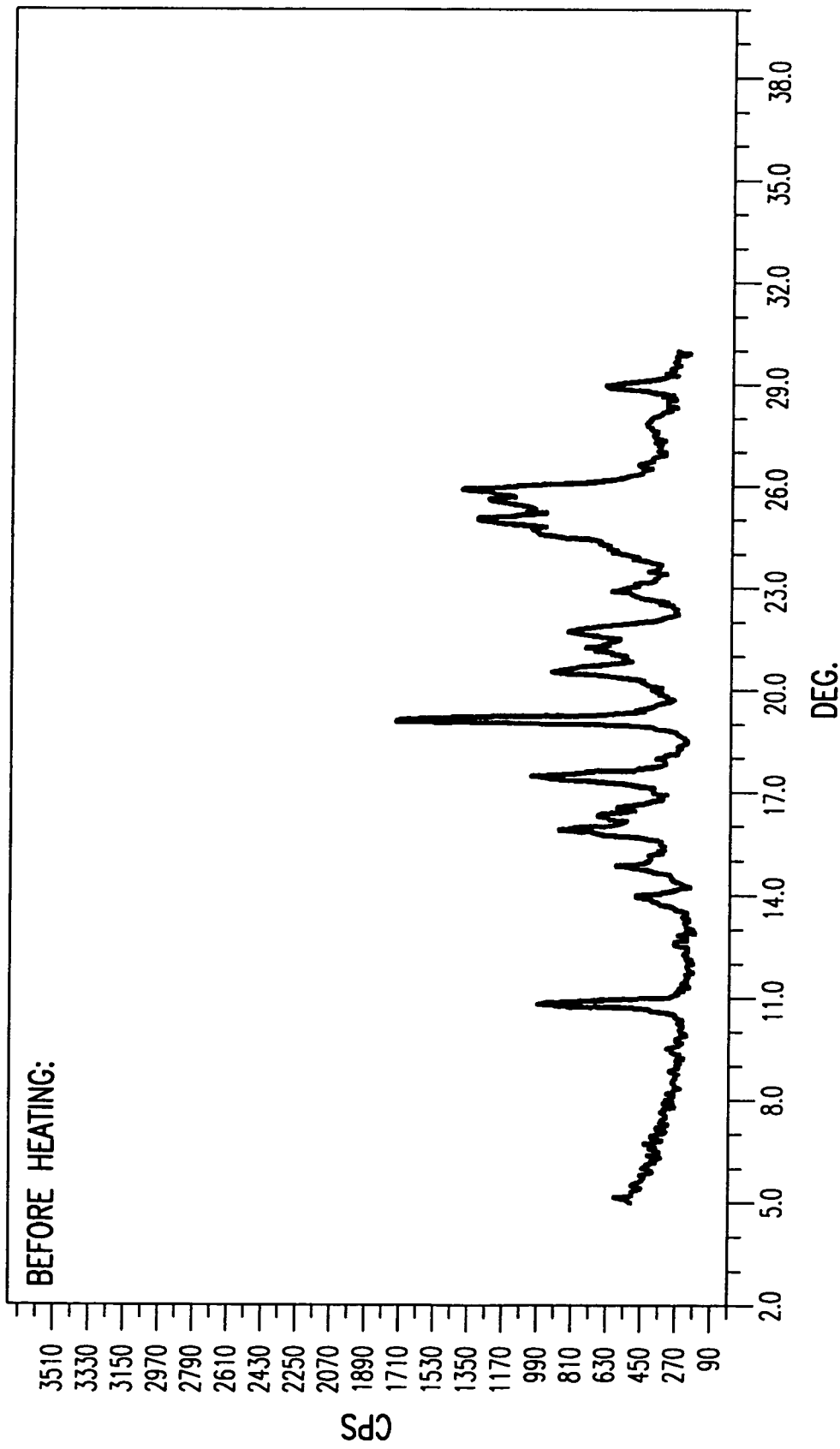
FIG. 7 is an X-Ray powder diffractograms of crystalline ziprasidone HCl Form A before and after heating.
Figure 7B:
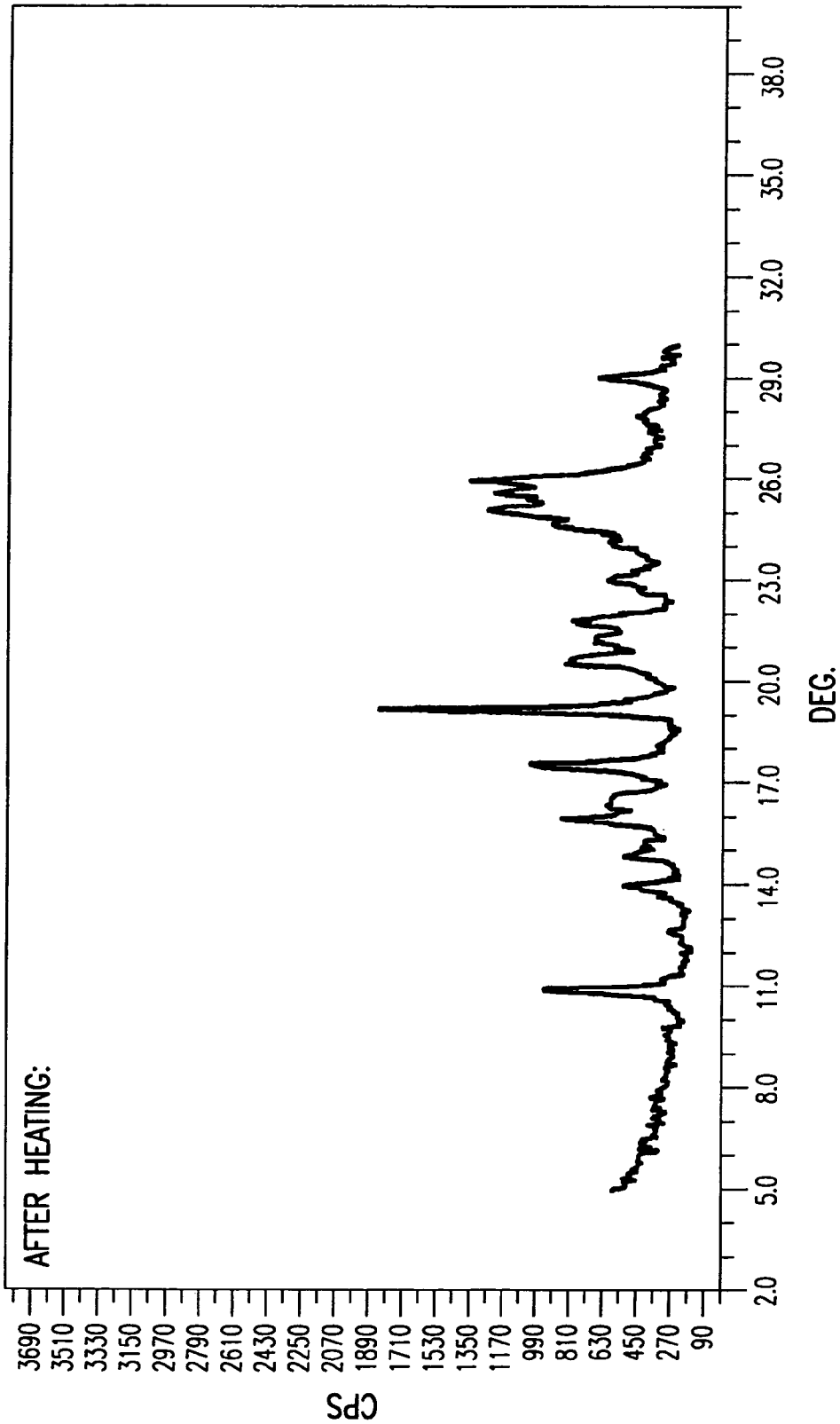

The crystalline ziprasidone HCl Form A of the present invention may be heated to a temperature of up to about 140° C. without a change in the crystal structure (see table 1 and FIG. 7).

TABLE NO. 1

Crystalline ziprasidone HCl forms heated at 80-105° C. overnight

| Original crystal form | Crystal form after heating at 80-105° C. overnight |
| --- | --- |
| Form A | Form A |
| Form M | Anhydrous |

Figure 8A:
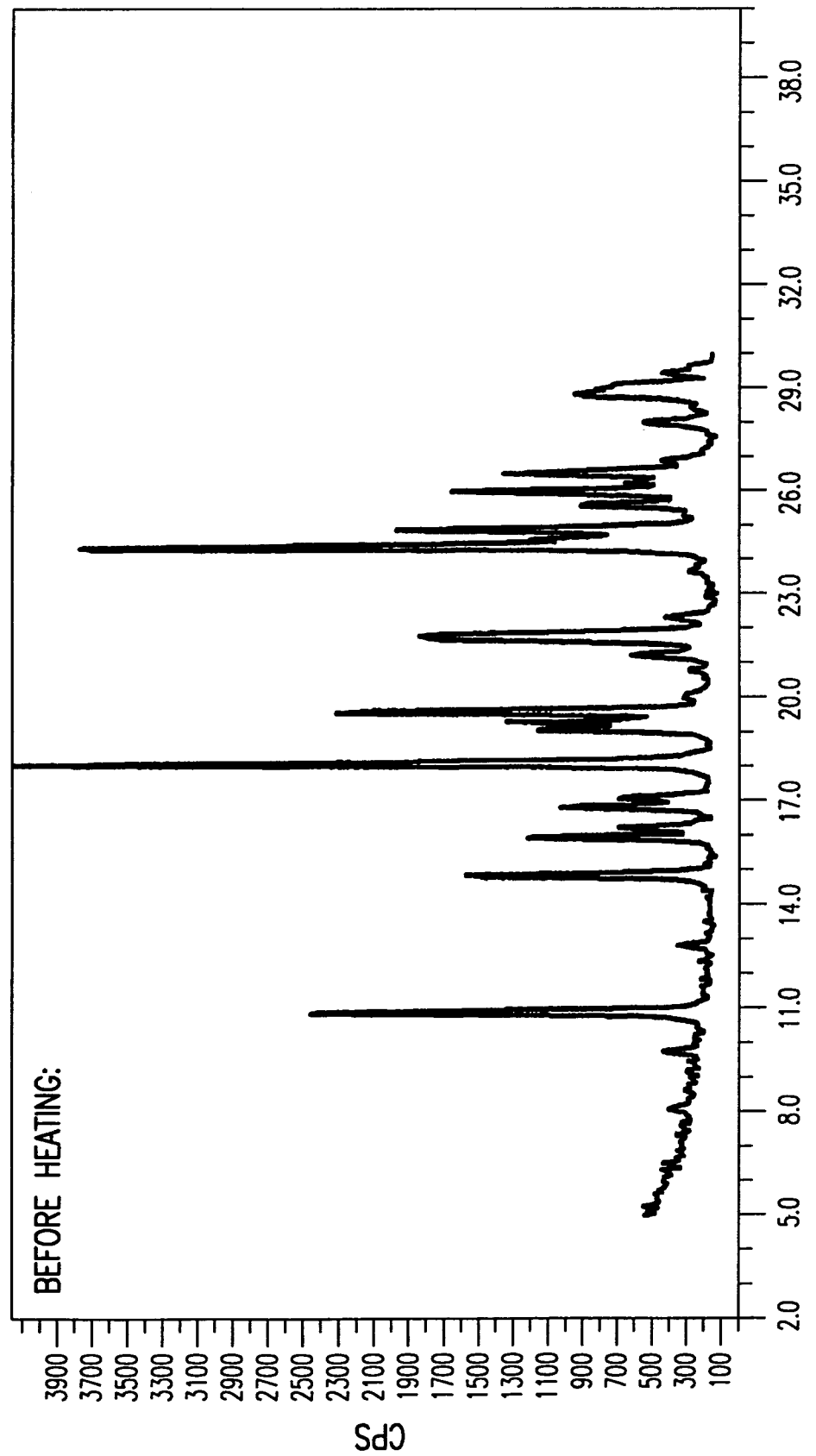
FIG. 8 is an X-Ray powder diffractograms of crystalline ziprasidone HCl Form M before and after heating.
Figure 8B:
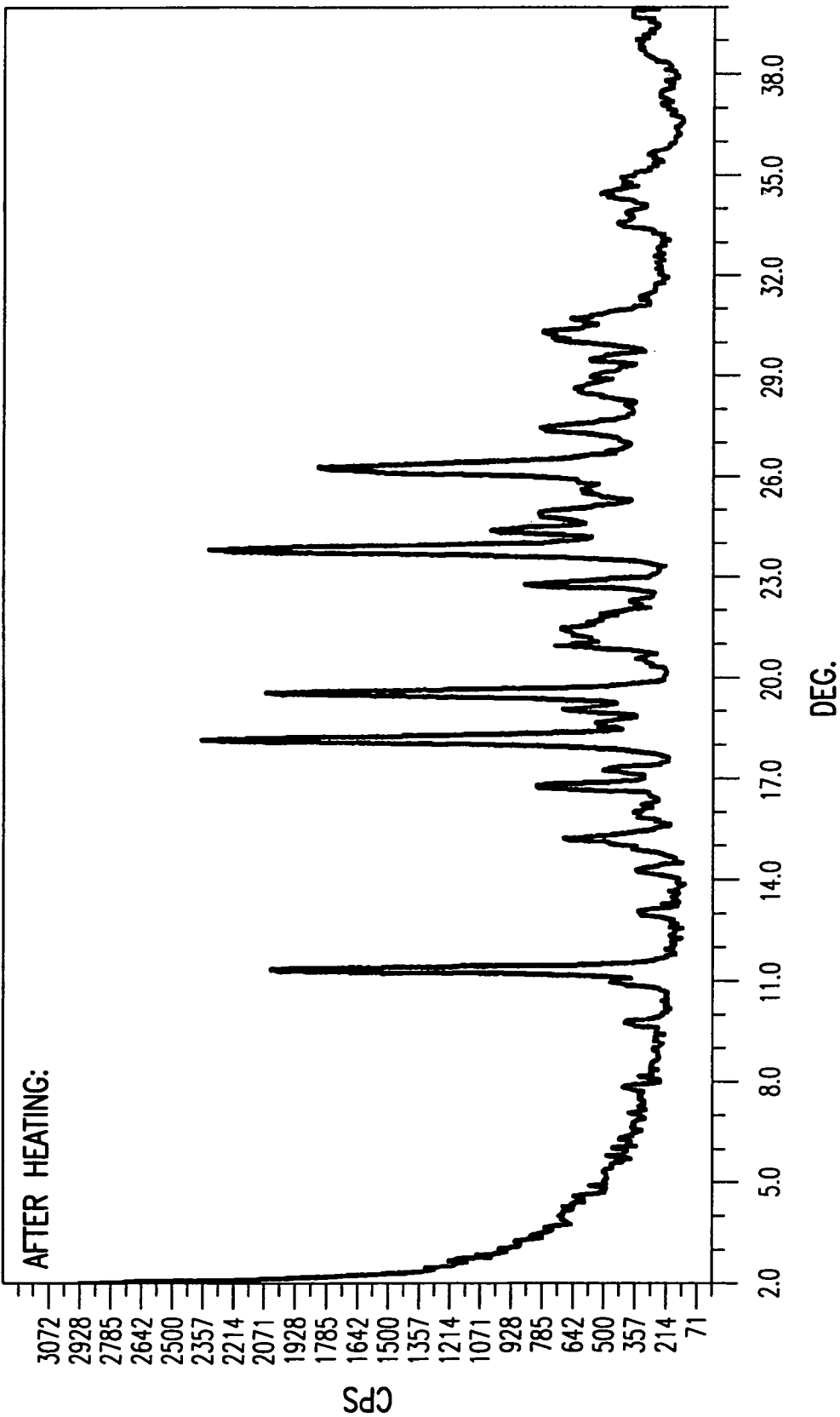
Figure 9A:
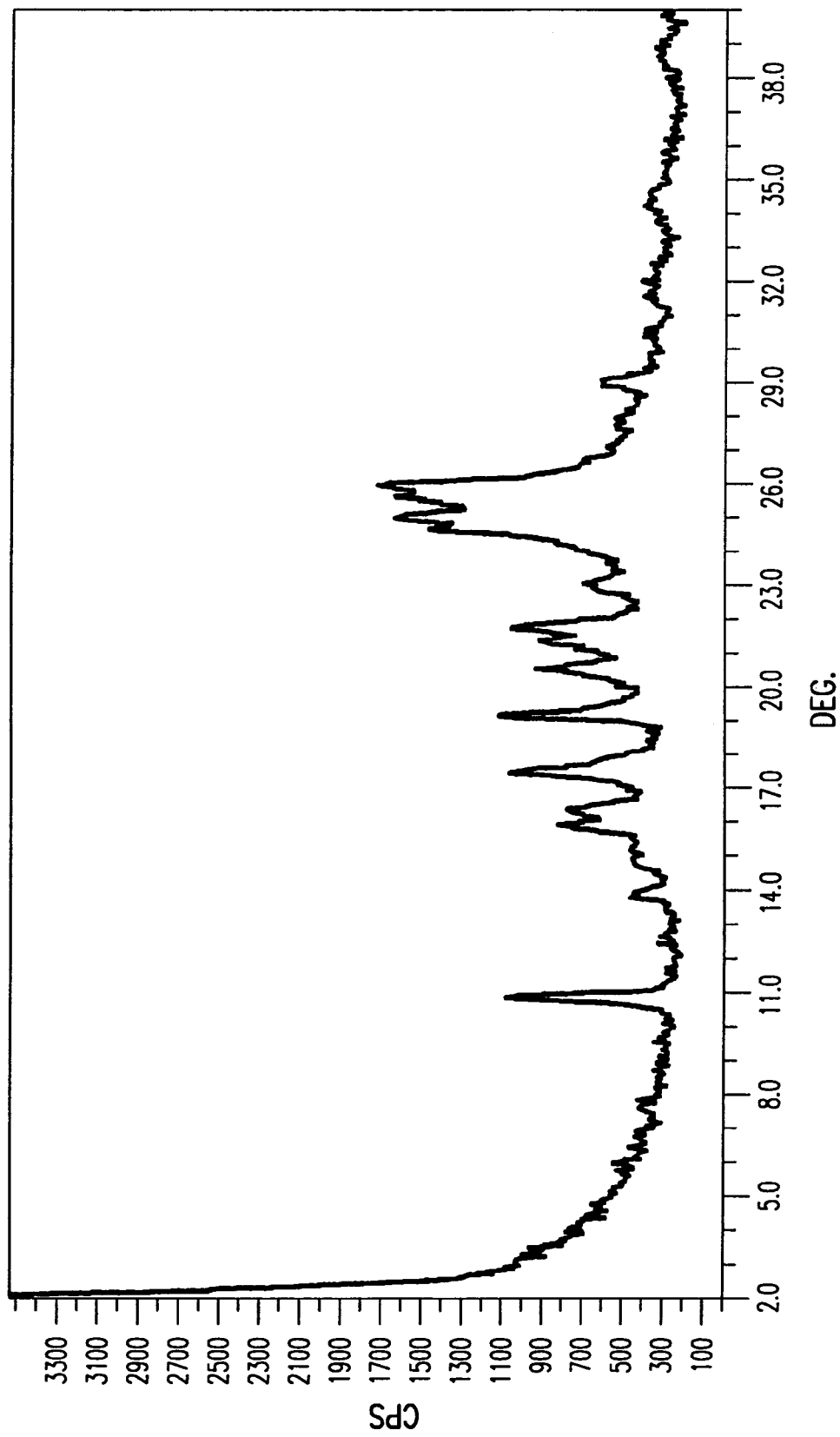
FIG. 9 is an X-Ray powder diffractograms of crystalline ziprasidone HCl Form A before and after storage at 0% relative humidity.
Figure 10A:
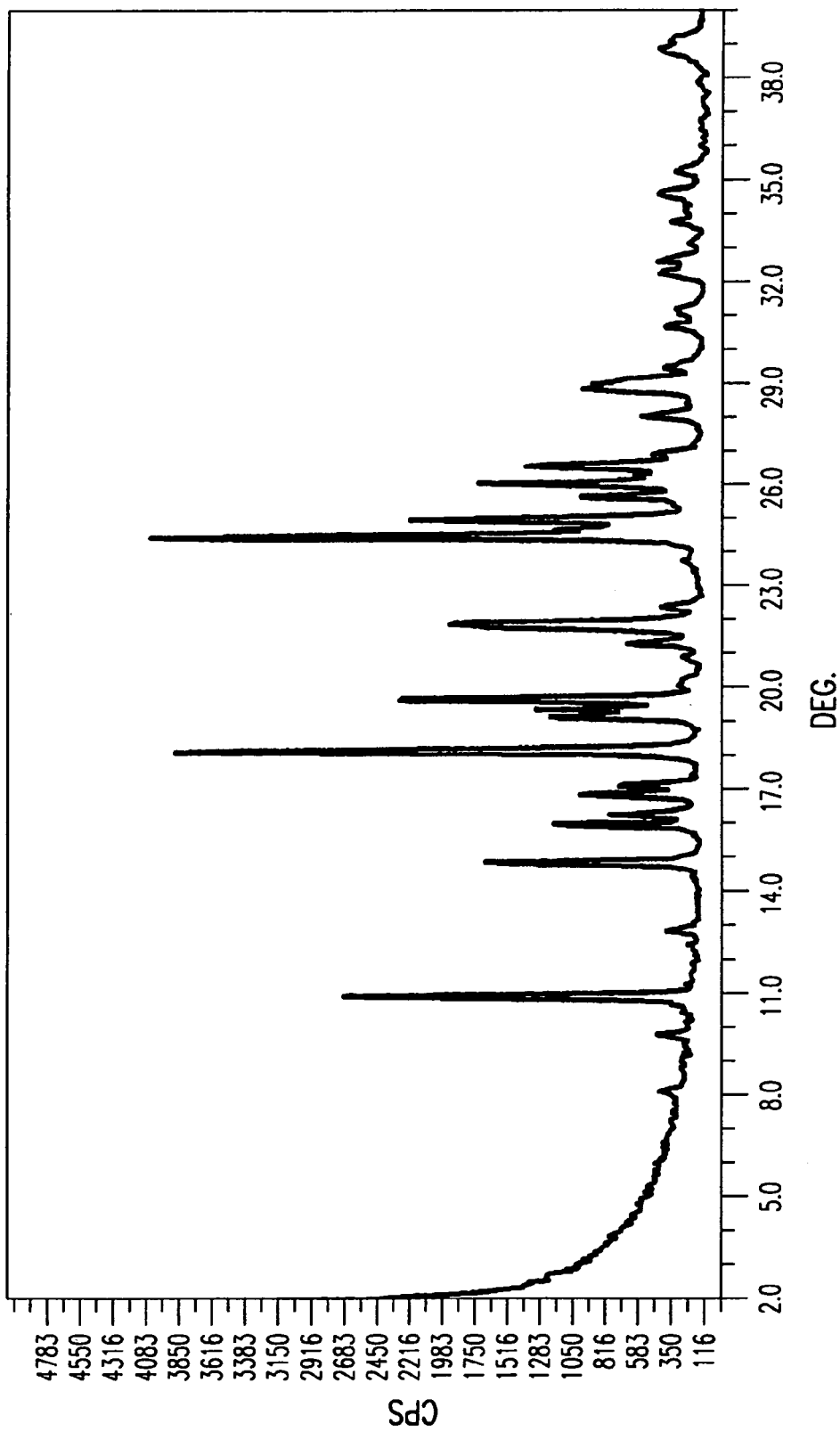
FIG. 10 is an X-Ray powder diffractograms of crystalline ziprasidone HCl Form M before and after storage at 0% relative humidity.
Figure 10B:
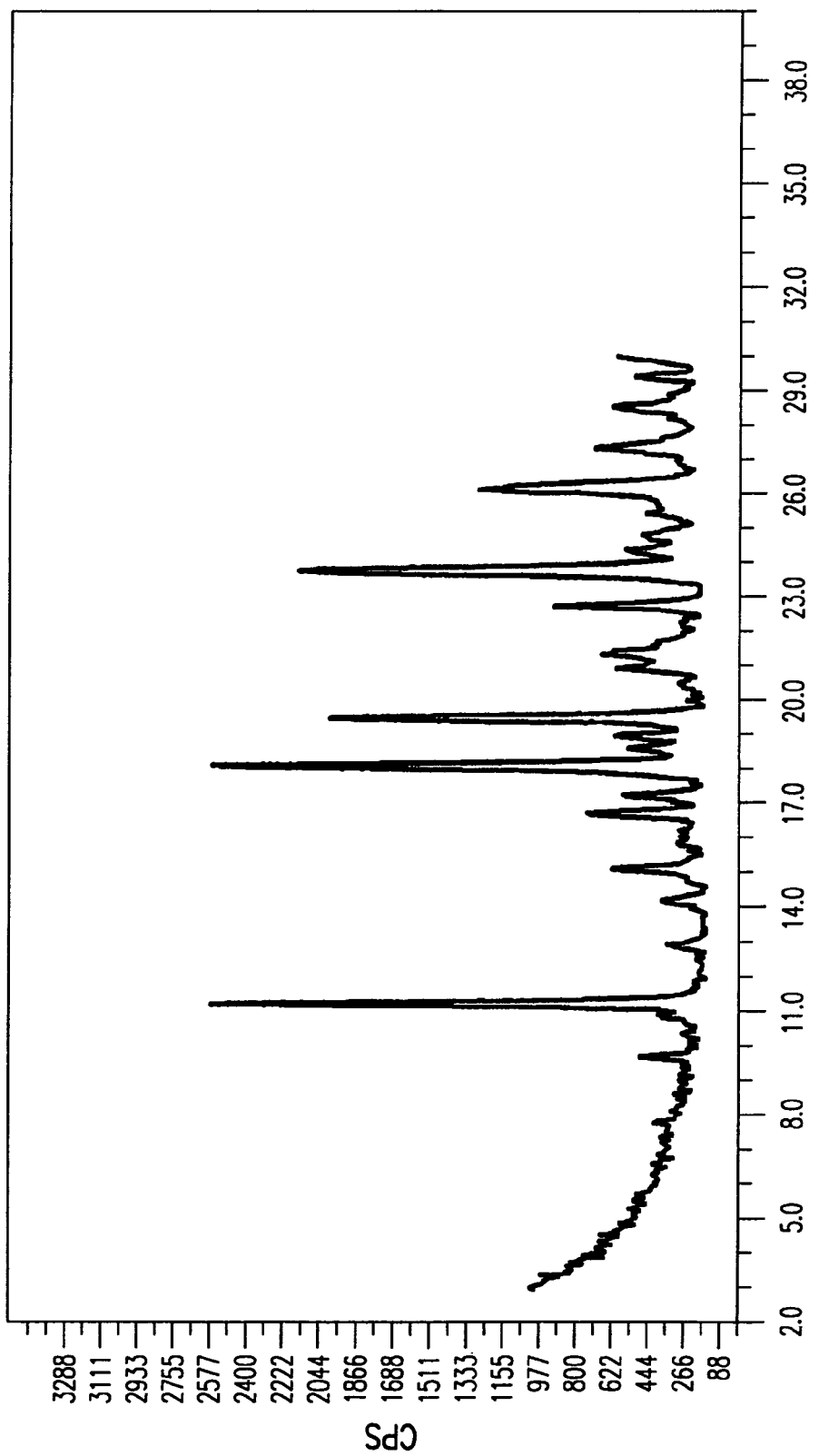
Figure 11:
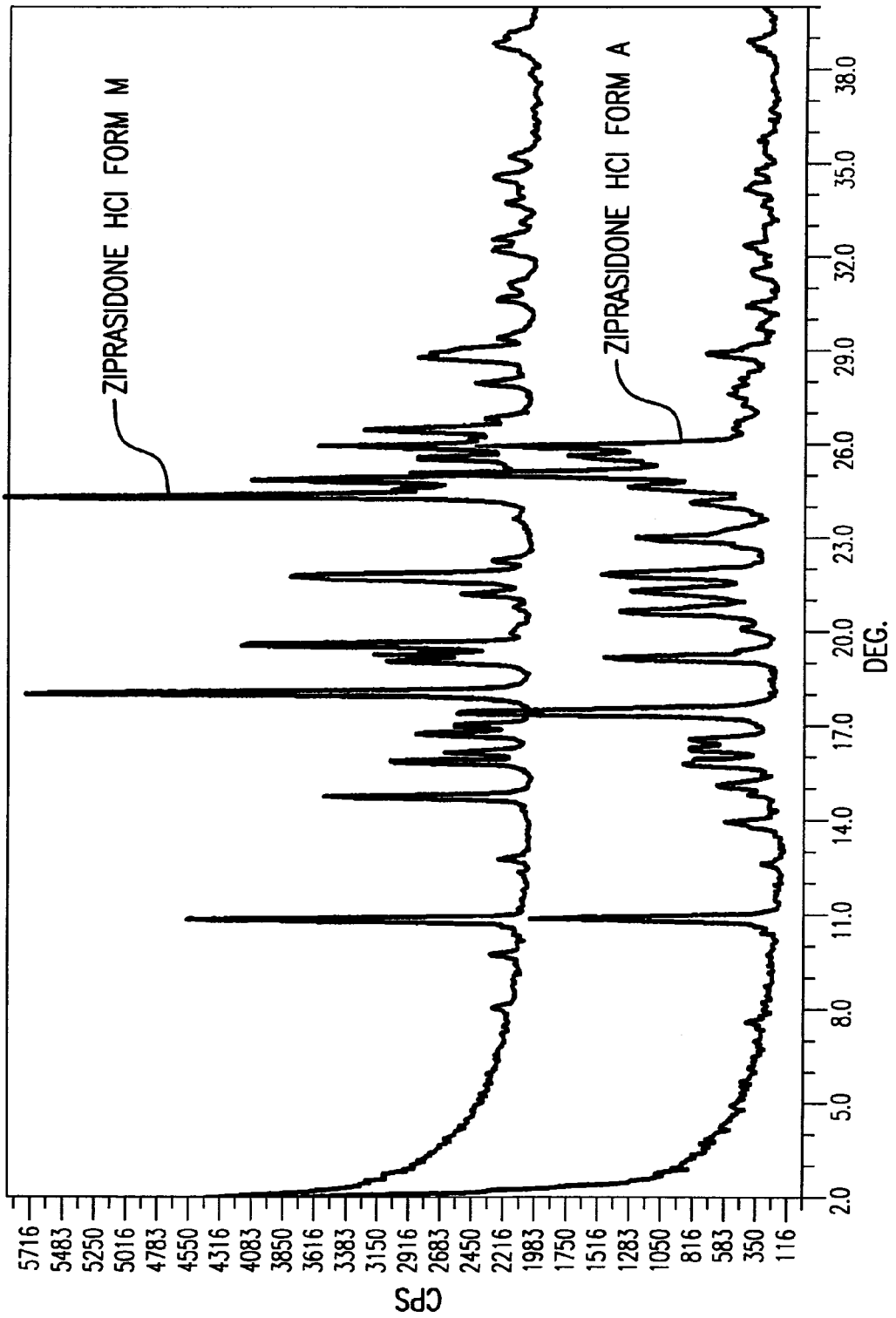
FIG. 11 is a comparison of XRD patterns of crystalline Ziprasidone HCl Form A and Ziprasidone HCl Form M.

The present invention provides a crystalline ziprasidone HCl Form A, of which no more than about 5% is transformed into Form M upon exposure at 0% humidity for prolonged periods (such as 3 weeks, see table 6 and FIG. 9), or storage under accelerated aging conditions (such as 40° C., 75% RH, see tables 2 and 3) for at least about 6 months. Ziprasidone HCl Form M, however, converts to the anhydrous form under heating (see table 1 and FIG. 8) or exposure to 0% relative humidity (see table 6 and FIG. 10).

TABLE NO. 2

Stability results

| Time Interval | Results | | |
| --- | --- | --- | --- |
| | 25° C. | 40° C. | 55° C. |
| t = 0 | A | | |
| 1 M | | A | A |
| 2 M | | A | A |
| 3 M | A | A | A |
| 6 M | A | A | A |

TABLE NO. 3

Stability results

| Time Interval | Results | | |
| --- | --- | --- | --- |
| | 25° C. | 40° C. | 55° C. |
| t = 0 | A + less than 5% M | | |
| 1 M | | A + less than 5% M | |
| 2 M | | A + less than 5% M | A + less than 5% M |
| 3 M | A + less than 5% M | A + less than 5% M | A + less than 5% M |
| 6 M | A + less than 5% M | A + less than 5% M | A + less than 5% M |

When slurried in water, no more than 5% Form A is transformed into Form M. However, in ethanol slurry, 95% of the crystalline ziprasidone transforms to Form M.

The crystalline ziprasidone HCl Form A provided in the present invention has a specific surface area (SSA) higher than about 4 m$^2$/g, more preferably higher than about 8, most preferably higher than about 11 such as about 14 as measured by BET. Preferably, the SSA is about 5 to about 20 m$^2$/g. The high SSA of the crystalline ziprasidone HCl is achieved by the rapid addition of HCl to the solution of ziprasidone base, and precipitation at a low temperature. The results are summarized in Table 4:

TABLE NO. 4

Specific surface area results

| Sample | Specific surface area [m²/g] | Crystal form |
|---|---|---|
| **Repetition of U.S. Pat. No. 6,150,366 Example 10 | 2.135 | M |
| **Repetition of U.S. Pat. No. 6,150,366 procedure (comparative example 15) | 3.908 | M |
| **Repetition of U.S. Pat. No. 5,312,925 Example 2 | 3.909 | M |
| **Sample prepared according to example 16 | 5.461 | A |
| **Sample prepared according to example 19 | 11.335 | A |
| *Sample prepared according to example 17 | 14.646 | A |
| *Sample prepared according to example 18 | 18.831 | A |

*cell volume = 12 cm³
**cell volume = 9 cm³

The crystalline ziprasidone HCl Form A provided in the present invention has a significantly higher specific surface area than Form M prepared by repeating the procedure disclosed in U.S. Pat. No. 5,312,925 and Example 10 in U.S. Pat. No. 6,150,366.

Crystalline ziprasidone HCl Form A may be prepared by providing a slurry of ziprasidone base, aqueous HCl and a solvent selected from the group consisting of toluene, monochlorobenzene, methanol, ethanol, diethyl-carbonate, water, isopropyl alcohol or mixtures thereof, and allowing the slurry to last for a sufficient time (maintaining) to obtain crystalline ziprasidone HCl Form A. When the solvent is a non-polar solvent or water, the combining/reacting is preferably carried out at a temperature of at least about 40° C., more preferably from about 50° C. to about 70° C., and most preferably at about 60° C. The combining with HCl is preferably carried out rapidly. The slurrying after the combining is preferably carried out at a temperature of about 20° C. to about 30° C., more preferably at about room temperature. Form A obtained by this process may have high crystallinity.

Crystalline ziprasidone HCl Form A can also be prepared by stirring a solution of ziprasidone base, a $C_{1-4}$ alcohol and an organic acid (such as a $C_1$ to $C_7$ carboxylic acid) at room temperature, then adding water and aqueous HCl to obtain crystalline ziprasidone HCl Form A. Preferably, the $C_{1-4}$ alcohol is either ethanol or methanol. Preferably, the organic acid is a $C_{1-4}$ carboxylic acid, more preferably the organic acid is acetic acid and formic acid.

The water content of crystalline ziprasidone HCl Form A can be increased by humidification.

Crystalline ziprasidone HCl Form A may also be prepared by slurrying another form of ziprasidone HCl in a suitable solvent such as tetrahydrofuran or ethanol. Preferred starting material is ziprasidone HCl Form E. The slurry is allowed to last for a sufficient time to obtain crystalline ziprasidone HCl, which may be recovered by techniques well known in the art such as filtration. The slurry temperature is preferably at least about 40° C. when using THF. Ziprasidone HCl Form E transforms to Form A when exposed to a relative humidity of about 20% to about 60% for about 22 days.

Ziprasidone HCl having a water content of about 4.6% to about 6.6% may be prepared by slurry of ziprasidone HCl Form E in THF. The temperature of the slurry is preferably less than about 40° C., more preferably about room temperature. The slurry is maintained preferably of about 12 hours to about 3 days. The wet solid may then be dried, for example at a temperature of about 40° C. to about 70° C., followed optionally by additional drying up to a temperature of preferably about 120° C., as illustrated in examples 20 and 21. The solid, if dehydrated, may then be put in a humid atmosphere, preferably more than about 50% humidity, more preferably more than about 80% humidity and most preferably about 100% humidity to obtain a hydrated crystal having a water content of about 4.6% to about 6.6% by weight.

Ziprasidone HCl Form M may be prepared by slurrying Form A in a $C_1$ to $C_4$ alcohol or acetic acid, preferably ethanol (preferably 95%), more preferably at a temperature of about reflux temperature and 20° C. below the reflux temperature, even more preferably about 10° C. below the reflux temperature to about reflux, and most preferably at about reflux temperature. About three hours at reflux temperature is sufficient to obtain a transformation.

The present invention also provides for preparing crystalline ziprasidone HCl Form A by exposing ziprasidone Form E to a relative humidity of about 20% to about 60% for about 22 days (see table 5).

TABLE NO. 5

Water uptake (%) and crystal form of ziprasidone HCl form E equilibrated at different relative humidities for 22 days

| RH (%) | TGA weight loss (%) | Crystal form |
|---|---|---|
| 0 | 5.3 | Amorphous |
| 20 | 7.2 | A |
| 40 | 4.8 | A |
| 60 | 5.0 | A |
| 80 | 9.2 | M + A |
| 100 | 51.3 | M + A + amorphous |

The present invention also provides for preparation of substantially pure crystalline ziprasidone HCl Form A. In this embodiment, crystalline ziprasidone HCl is prepared by fast crystallization through addition of HCl to a slurry or solution of ziprasidone base in a solvent such as water, a $C_1$ to $C_4$ linear or branched alcohol, or mixtures thereof. An IPA/water ratio of about 2:1 to about 0:20 (v/v) is an appropriate solvent for preparation of substantially pure crystalline ziprasidone HCl Form A. Suitable temperature for the reaction is from about 0° C. to about 40° C. A suitable HCl quantity is from about 2 to about 8 equivalents. Preferably, the HCl is added at a fast rate. The addition rate is temperature related: at room temperature, the rate is preferably about 5 to about 30 minutes, more preferably about 5 to about 20 minutes, most preferably about 5 to about 10 minutes; at a lower temperature, the addition rate is preferably about 5 to about 60 minutes, more preferably about 5 to about 30 minutes. The addition may also be carried out in reverse, i.e., addition of ziprasidone base slurry/solution to HCl.

One of skill in the art would appreciate that as the slurry is allowed to last for a sufficient time to obtain a particular polymorphic form, the slurry may dry up due to for example evaporation of the solvents. As the examples illustrate, additional amounts of a solvent may be added (same or different solvent), preferably followed by stirring, to obtain a slurry.

A slurry is most effective when the solids of the heterogeneous mixture are in substantial contact with the solvent. When the solids settle down, the efficiency of the slurry process often decreases due to a decrease in contact. Thus, one of skill in the art would appreciate that if during the slurry process the solids settle down, a force such as stirring or agitating may be applied to disperse the solid. Even when the solids have not settled down, bringing of movement in the solvent may even further increase the efficiency of the slurry process.

Crystalline ziprasidone HCl Form A may be recovered from the slurry by conventional techniques in the art such as decanting, filtration and centrifugation.

The present invention also provides solid crystalline ziprasidone HCl having a water content of about 4.6% to about 6.6% by weight. This crystalline form may be sesquihydrate. No more than 5% of the solid crystalline ziprasidone HCl of the present invention transforms into Form M during exposure to 0% relative humidity (see table 6). The present invention further provides a solid crystalline ziprasidone HCl, of which no more than 5% transforms into Form M upon storage at 25, 40 and 55° C. for at least 3 months, preferably for at least 6 months (see table 7). This solid crystalline ziprasidone HCl has a specific surface area (SSA) higher than 4 $m^2/g$, and preferably between 5 and 20 $m^2/g$.

TABLE NO. 6

Water uptake (%) and crystal form of crystalline ziprasidone HCl forms equilibrated at 0% relative humidity

| Original crystal form | Crystal form upon storage at 0% relative humidity |
|---|---|
| Form A | Form A |
| Crystalline ziprasidone HCl having a water content of 4.6-6.6% | Crystalline ziprasidone HCl having a water content of 4.6-6.6% |
| Form M | Anhydrous |

TABLE NO. 7

Stability results

| Time Interval | Results | | |
|---|---|---|---|
| | 25° C. | 40° C. | 55° C. |
| t = 0 | Cryst. ZPR HCl (4.6-6.5% water) | | |
| 1 M | | Cryst. ZPR HCl (4.6-6.5% water) | Cryst. ZPR HCl (4.6-6.5% water) |
| 2 M | | Cryst. ZPR HCl (4.6-6.5% water) | Cryst. ZPR HCl (4.6-6.5% water) |
| 3 M | Cryst. ZPR HCl (4.6-6.5% water) | Cryst. ZPR HCl (4.6-6.5% water) | Cryst. ZPR HCl (4.6-6.5% water) |
| 6 M | Cryst. ZPR HCl (4.6-6.5% water) | Cryst. ZPR HCl (4.6-6.5% water) | Cryst. ZPR HCl (4.6-6.5% water) |

Pharmaceutical formulations of the present invention contain crystalline ziprasidone HCl, such as one of those disclosed herein, or ziprasidone HCl amorphous, optionally in mixture with other form(s) of ziprasidone. In addition to the active ingredient(s), the pharmaceutical formulations of the present invention may contain one or more excipients. Excipients are added to the formulation for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, ziprasidone and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

The dosage of GEODON may be used as guidance. The oral dosage form of the present invention is preferably in the form of an oral capsule having a dosage of about 10 mg to about 160 mg, more preferably from about 20 mg to about 80 mg, and most preferably capsules of 20, 40, 60 and 80 mg.

Instrumentation:

X-Ray powder diffraction data were obtained using by method known in the art using a SCINTAG powder X-Ray diffractometer model X'TRA equipped with a solid state detector. Copper radiation of 1.5418 Å was used. A round aluminum sample holder with round zero background quartz plate, with cavity of 25(diameter)*0.5(dept) mm. Detection limit: 5%.

TGA analysis was done using a Mettler M3 meter. The weight of the samples was about 10 mg; the samples were scanned at a rate of 10° C./min from 25° C. to 200° C. The oven was constantly purged with nitrogen gas at a flow rate of 40 ml/min. Standard 70 µl alumina crucibles covered by lids with 1 hole were used.

IR analysis was done using a Perkin Elmer SPECTRUM ONE FT-IR spectrometer in DRIFTt mode. The samples in the 4000-400 $cm^{-1}$ interval were scanned 16 times with 4.0 $cm^{-1}$ resolution.

The water content of ziprasidone HCl was measured by the methods known in the art like Karl Fisher or thermogravimetric analysis (TGA). The TGA of the crystalline ziprasidone HCl matched with the Karl Fisher analysis. Water content is measured as percent w/w.

Specific surface area measurement:
Instrument: Coulter SA3100
Degassing: without
Sensitivity: high
Calculation: BET
Type: multipoint
Points: 10
Sample cell: 9 and 12$cm^3$ Ziprasidone free base used for preparations of the crystal forms of ziprasidone HCl may be, but is not limited to Form B. Ziprasidone base Form B is characterized by X-Ray peaks at 12.1, 15.2, 16.3, 18.4, 25.0 degrees 2 theta and is further characterized by XRD peaks at 5.2, 10.4, 11.3, 13.1, 21.1, 22.1. The ziprasidone free base has a DSC thermogram in which 17 and 120 J/g endothermic peaks can be seen at 92 and 220° C. The first corresponds to dehydration, the second to melting of the ziprasidone free base. The water content of the sample of the base is about 1.2% by weight. The Loss on Drying by TGA is about 2.1% by weight. One of skill in the art would appreciate that the processes of the present invention may use other forms of ziprasidone base as starting material.

EXAMPLES

Example 1

Preparation of Ziprasidone Base

Ziprasidone base for the experiments below was prepared according to the procedure "EXPERIMENT" in U.S. Pat. No. 5,312,925, column 4. The water content of the base was 1.2% (Karl Fisher).

Example 2

Preparation of Ziprasidone Base Form B

Ziprasidone base (50 g) and toluene (250 ml) were charged into a 0.5 L three necked flask. The obtained slurry was heated at 85° C. for 2 hours. The hot slurry was filtrated and the solid was washed with methanol. The solid was dried in air-circulated oven at 50° C. to afford the dried Ziprasidone base form B (by XRD) (45.39 g).

Example 3

Preparation of Crystalline Ziprasidone HCl Form A in Toluene from Ziprasidone Base Form B and Aqueous HCl Ziprasidone base Form B (10 g) and toluene (200 ml) were heated to reflux, and the slurry was cooled to ~65° C. At 65° C., aqueous HCl 37% (10 ml) was added and the slurry was stirred at room temperature over night. The solid was a sticky material; to which water was added (100 ml). The solid was then filtered and washed with toluene. The wet solid was crystalline ziprasidone HCl as confirmed by XRD. The product was dried in an oven at 50° C. The dried solid was crystalline ziprasidone HCl Form A, (10.64 g) as confirmed by XRD. (The water content was 4.7% by K.F.).

Example 4

Preparation of Crystalline Ziprasidone HCl Form A in Monochlorobenzene/Methanol from Ziprasidone Base Form B and Aqueous HCl To a slurry of ziprasidone base Form B (10 g) in monochlorobenzene (100 ml) was added aqueous HCl (37%) (10 ml) at room temperature and the stirring was continued at room temperature over night. A sticky solid was formed, to which methanol (50 ml) was added, followed by stirring for an additional 4 hours. The solid was filtered and washed with methanol. The wet product was crystalline ziprasidone HCl as confirmed by XRD. After drying at 50° C. for about 16 hours, crystalline ziprasidone HCl Form A was obtained (10.37 g) as confirmed by XRD (The water content was 4.17% by K.F.).

Example 5

Preparation of Crystalline Ziprasidone HCl Form A in Water from Ziprasidone Base Form B and Aqueous HCl 3M Ziprasidone base Form B (10 g) was added to a 3M solution of HCl (50 ml HCl (37%) in 150 ml HPLC grade water) and the slurry was heated at 60° C. The reaction mixture was then stirred at 60° C. for 18 hours. After cooling to room temperature, a solid was filtered and washed with water. The material was dried in an oven at 50° C. for 16 hours. The wet solid and the dried solid were crystalline ziprasidone HCl Form A (the water content of the dried solid is 4.88% by K.F.), as confirmed by XRD.

Example 6

Preparation of Crystalline Ziprasidone HCl Form A in Isopropyl Alcohol from Ziprasidone Base Form B and Aqueous HCl Hydrochloric acid (37%) (10 ml) was added to a slurry of ziprasidone base Form B in isopropyl alcohol (IPA) (100 ml). The slurry was stirred at room temperature over night. A solid was filtered, washed with IPA and dried at 50° C. for 16 hours. The dried solid was crystalline ziprasidone HCl Form A (The water content of the dried solid is 4.01% by K.F.), as confirmed by XRD.

Example 7

Preparation of Ziprasidone HCl Form E from Ziprasidone Base Form B in Acetonitrile and Aqueous HCl Aqueous HCl (37%) (10 ml) was added to a slurry of ziprasidone base Form B (10 g) in acetonitrile (200 ml) at reflux. After the addition, the slurry was heated over night. A solid was filtered and washed with acetonitrile. After drying at 50° C. for ~16 hours, ziprasidone HCl Form E was obtained (12.71 g) (The water content was 9.25% by K.F. and the loss on drying by TGA is 18.8%), as confirmed by XRD.

Example 8

Preparation of Ziprasidone HCl Monohydrate (M) from Ziprasidone HCl Form A

Crystalline ziprasidone HCl Form A (10 g) was heated in ethanol 95% (200 ml) at reflux for 3 hours. The hot slurry was filtered to obtain a solid. The solid was washed with hot ethanol (10 ml×4). Part of the wet solid was dried at 50° C. for 16 hours and the other part at 45° C. under vacuum. The wet and dried solids were ziprasidone HCl Form M (the monohydrate) (The water content of the dried solids was 4.25 and 4.24% (by K.F) and the loss on drying by TGA are 4.6%.), as confirmed by XRD.

In all the above examples, drying was carried out in an air-circulated oven.

Example 9

Preparation of Crystalline Ziprasidone HCl Form A by Slurry of Ziprasidone HCl Form E 1) Ziprasidone HCl Form E (2 g) in ethanol 95% (20 ml) was stirred at room temperature for 24 hours. A solid was filtered, washed with ethanol (95%) and dried at 50° C. in an air-circulated oven. The dried solid was crystalline ziprasidone HCl Form A (K.F. 5.16).

The same result as was obtained when the temperature during the slurry was 50° C. (K.F. 5.06%).

2) Crystalline ziprasidone HCl Form A was obtained by slurry of Form E in ethanol with various water contents (from 5% to 30%) (K.F. 5.16%) at room temperature or at 50° C. (K.F. 5.06% and 4.99%) or by slurry of Form E in THF containing water at a temperature between room temperature and 50° C. For example, the slurry of E in THF containing 40% water at 50° C. gave crystalline ziprasidone HCl Form A (K.F. 4.76%).

Example 10

Preparation of Crystalline Ziprasidone HCl Form A with High Crystallinity from Ziprasidone Base in Diethyl-carbonate/aq. HCl To the slurry of ziprasidone base (10 g) (Form B) in diethyl-carbonate (250 ml) at 60° C. was added concentrated aqueous HCl (10 ml); then the slurry was stirred at room temperature for about 16 hours. Water (50 ml) was added and the stirring was continued for an additional three hours. A solid was filtered, washed with water (2×20 ml) and dried in an air-circulated oven for 16 hours. The wet and the dried solid was crystalline ziprasidone HCl (K.F. 4.16%). The dried solid was Crystalline ziprasidone HCl Form A with high crytsallinity.

Example 11

Preparation of Substantially Pure Crystalline Ziprasidone HCl Form A

1) Preparation of Crystalline Ziprasidone HCl from Isopropyl-Alcohol:Water

In a 250 ml reactor were charged ziprasidone base (10 g) and a 1:1 mixture of isopropylalcohol-water (100 ml), and the mixture was cooled to 10° C. To the above slurry, aqueous HCl (32%) was added during 5 minutes, while maintaining the temperature less than 15° C. The obtained slurry was than stirred at 10-15° C. for 15 hours, and a solid was isolated by filtration, washed with IPA-water and dried at 50° C. under vacuum. The XRD of the dried material (10.79 g), which lacked the peak at 18.1, characteristic of Form M, indicates that the product was crystalline ziprasidone HCl Form A substantially free of Form M (water content by K.F. is 4.85%).

2) Preparation of Crystalline Ziprasidone HCl Form A from Water

To the slurry of ziprasidone base (10 g) in water (100 ml) at room temperature, aqueous HCl (10 ml) (32%) was added over 10 minutes. The slurry was then stirred at room temperature for 5 hours. The solid was filtered, washed with water and dried on table, followed by drying at 50° C. The XRD of the solid, which lacked the peak at 18.1, characteristic of Form M, showed the product was crystalline ziprasidone HCl Form A substantially free of Form M (water content by K.F. 5.04).

3) Preparation of Crystalline Ziprasidone HCl Form A from IPA-Water by Reverse Addition A slurry of ZPR base (5 g), 25 ml IPA and 25 ml water was prepared in a 250 ml reactor. This slurry was dropped into a flask containing (32%) aqueous HCl (10 ml) at room temperature. During the addition, the temperature rose to ~35° C. The slurry was than stirred at room temperature 24 hours. The solid was filtered, washed with mixture water-IPA and dried at 50° C. The XRD of the dried solid (7.2 g), which lacked the peak at 18.1, showed the material was crystalline ziprasidone HCl Form A substantially free of Form M (water content by K.F. 4.89).

Example 12

Preparation of Form M from Crystalline Ziprasidone HCl Form A

The slurry of crystalline ziprasidone HCl Form A (30 g) and acetic acid (510 ml) was heated at 60° C. for 2 h. The mixture was than cooled to room temperature and the solid was filtered and washed with acetic acid (2×30 ml). After drying at 50° C. ziprasidone HCl Form M was obtained (28.37 g). (Water content by K.F. 3.95%).

Example 13

Preparation of Ziprasidone HCl Form A in Humid Air Fluidized Bed Drier

1) Precipitation from Solution 60 gr of Ziprasidone-base Cryst, 480 ml of Ethanol 95% and 300 ml of Acetic Acid were fed into a 1 liter stirred glass beaker at 25° C. The stirrer was turned on, and the mixture was stirred for 20 min until the Ziprasidone-base dissolved completely. 6 gr of "Eno" type Active Carbon were fed into the beaker, and the solution was Carbon treated for 30 min at 25° C. The used Carbon was removed by filtering the treated solution under reduced pressure through a No.1 Whattman filtration paper.

The used carbon was washed with 120 ml 95% Ethanol, and the wash filtrate was added to the filtered solution, both were fed into a 1 liter stirred glass reactor. 300 ml of treated Water were added into the reactor, and the solution was cooled to 0° C. 120 ml 10% w/w aqueous Hydrochloric acid solution was added drop wise into the reactor during 10 min. During the acid addition, Ziprasidone-hydrochloride precipitated. After the acid addition was completed, the slurry was stirred at 0° C. for additional 30 min.

The crystals were isolated by filtering the slurry under reduced pressure through a No. 1 Whattman filtration paper. After drainage of the mother liquor, The wet cake was washed with 120 ml aqueous mixture consisting of 50% Ethanol 95%. After the wash liquor was completely drained, the wet cake was washed with 300 ml of water. The wet filter cake was washed four additional times, each time with 300 ml (total 1500 ml) until pH~5 was obtained (the same pH as the pH of the fresh Water).

120 gr of wet Ziprasidone-HCl crystals were obtained.

The wet crystals were tested by XRD and found to be ziprasidone HCl Form A.

The wet crystals were dried at 50° C. for 60 hrs, until the water content was 0.75%.

2) Humidification 20 gr of the dried product were humidified in a humid air fluidized bed drier ("Mini-Glatt"). The dry air inlet temperature was 50° C. After the water spray, the air temperature was 16° C.

After 30 min, the water content in the product was 5.77% The humid product was discharged.

Example 14

Preparation of High Crystallinity Ziprasidone HCl Form A from Ziprasidone Base in IPA/Water/HCl Into a 250 ml flask were charged ZPR base (10 g), water (50 ml) and IPA (50 ml). To the obtained slurry HCl 32% (20 ml) was added during 0.5 h. The temperature rose from room temperature to about 30° C. The stirring was continued for 20 h at room temperature; after this the solid was filtrated, washed twice with a mixture IPA-water 1:1 (10 ml) and dried in vacuum oven at 50° C. The dried solid was high crystallinity ziprasidone HCl Form A (by XRD). (The water content is 4.89 by K.F.)

Example 15

Comparative Example: Preparation of Ziprasidone HCl Form M from THF:H$_2$O (from U.S. Pat. No. 6,150,366)

Into a 250 ml reactor, Ziprasidone base (3 g), THF (90 ml) and H2O (9 ml) were charged. As the reactor was heated to reflux (64° C.), Ziprasidone dissolved, forming a clear, dark solution. The temperature was lowered to 60° C. and stirring to 103 rpm. HCl 11% was added until turbidity was observed. This turbid solution was left under stirring at 60° C. for 50 min., and the rest of 9 g HCl 11% was added dropwise during 30 min.

The slurry was cooled to 13° C., kept at this temperature for 1 h 40 min., filtrated, and washed with two portions of 3 ml THF. The solid was dried at 23° C. overnight. The dried solid was crystalline ziprasidone HCl Form M (by XRD). Specific surface area 3.908 m2/g Example 16

Preparation of Ziprasidone HCl Form A from EtOH:H$_2$O

A 150 ml reactor equipped with mechanic stirring was charged with Ziprasidone base (3 g), EtOH abs. (15 ml) and H$_2$O (15 ml), cooled to 15° C., and a slurry was obtained. slurry. HCl 21% (4.55 ml) were added dropwise during 10 min. After the addition the slurry is left at the same temperature overnight. The slurry was then filtered, washed with EtOH:H$_2$O (10 ml), and dried at 65° C. under vacuum. The dried solid was crystalline ziprasidone HCl Form A (by XRD). Specific surface area: 5.461 m$^2$/g Example 17

Preparation of Ziprasidone HCl Form A from IPA:H$_2$O at Room Temperature

A 50 ml flask equipped with mechanic stirring was charged with Ziprasidone (3.5 g), IPA (17.5 ml) and H$_2$O (17.5 ml), and a slurry was obtained.

HCl 32% (3.33 ml) was added dropwise during 2 min, and the temperature was raised from 25 to 29° C. After addition, the slurry was left overnight, while stirring. The slurry was then filtrated, washed with IPA:H$_2$O 1:1 (7 ml) and dried at 65° C. under vacuum. The dried solid was crystalline ziprasidone HCl Form A (by XRD). Specific surface area: 14.646 m$^2$/g Example 18

Preparation of Ziprasidone HCl Form A from IPA:H$_2$O at 9° C.

A flask was charged with Ziprasidone (4.9 g), IPA (12.5 g) and H$_2$O (12.5 g), and was cooled in ice bath. When the temperature reached 9° C., HCl 21% (7.7 ml) was added dropwise during less than 5 minutes. The temperature was raised to 13° C., and the slurry was left, while stirring, at room temperature overnight. The slurry was then filtered, washed with IPA and dried at 50° C. under vacuum. The dried solid was crystalline ziprasidone HCl Form A (by XRD). Specific surface area: 18.831 m$^2$/g.

Example 19

Preparation of Ziprasidone HCl Form A from Acetic Acid/Ethanol

Ziprasidone base (11.2 g) was dissolved in EtOH (112 ml) and Acetic acid (78.2 ml). The solution was treated with active charcoal at 0° C. for color improvement during 30 min and filtrated. The solution was cooled back to 0° C., and HCl 32% (10 ml) was added. 30 min after the addition, the slurry was filtered and the solid dried at 50° C. under vacuum. The dried solid was crystalline ziprasidone HCl Form A (by XRD). Specific surface area: 11.335 m2/g.

Example 20

Preparation of Crystalline Ziprasidone HCl having a Water Content of 4.6-6.6% by Slurry of Ziprasidone HCl Form E Ziprasidone HCl Form E was stirred in tetrahydrofuran (20 ml) at room temperature for 23 hours. A solid was filtrated, washed with THF and dried at 60° C. in an air-circulated oven. The dried solid was crystalline ziprasidone HCl (K.F. 4.57%).

Example 21

Preparation of Ziprasidone HCl having a Water Content of 4.6-6.6% from Acetic Acid/Ethanol Crystalline ziprasidone HCl was prepared according to ex. 20. The wet solid was dried at 50° C. for about 16 hrs in vacuum oven, followed by an additional drying operation in vacuum-oven at 105° C. for 48 hrs. After drying, the solid contained 1.3% water (by Karl-Fischer).

The above dried material was kept in a chamber with RH 100% at 40° C. for 7 days. After this period of time the water content was 6.6% (by Karl-Ficher).

Example 22

Preparation of Ziprasidone HCl Form A from Acetic Acid/Ethanol

Ziprasidone base (15 g) was dissolved in a mixture of ethanol (150 ml) and acetic acid (75 ml). The solution was treated with basic alumina (1.5 g) for half hour. The discolored solution was filtrated and cooled to ~10° C. Aqueous HCl (10%, 30 ml) was added during 3 min. at the chilled solution (10° C.). The stirring was continued for additional 10 min. at 10° C. The obtained solid was filtrated, washed with water to pH 4 and dried in vacuum-oven at 50° C. for about 4 days. The obtained dried solid contained 0.53% water (by K.F.).

Example 23

Preparation of Ziprasidone HCl Form A from AcOH/MeOH/Water

Ziprasidone base (5 g) was dissolved in a mixture of acetic acid (25 ml), methanol (47.5 ml) and water (2.5 ml); the obtained solution was treated with active carbon (10% w/w) and tonsil (10% w/w). The solution was filtrated, diluted with water (25 ml) and cooled to 10° C. While the temperature reached 10° C. 10% HCl was added (10 ml) over 5 minutes. The stirring was continued for 40 min., then the solid was filtrated and washed with water and then with a mixture of MeOH/water. The solid obtained after drying was crystalline ziprasidone HCl form A.

Other similar procedures are shown in the following table:

| Example | Solvents | Ratio solvents | Ziprasidone form |
|---|---|---|---|
| 24 | AcOH:EtOH:water | 3:6:3 | A |
| 25 | AcOH:EtOH | 5:10 | A |
| 26 | AcOH:EtOH | 3:20 | A |
| 27 | AcOH:EtOH | 5:10 | A |
| 28 | AcOH:water | 5:15 | A |
| 29 | HCOOH:MeOH | 3:17 | A |
| 30 | HCOOH:MeOH | 3:10 | A |
| 31 | HCOOH:MeOH:water | 3:3:6 | A |
| 32 | HCOOH:MeOH:water | 6:6:12 | A |
| 33 | HCOOH:MeOH:water | 1.7:1.7:3 | A |
| 34 | HCOOH:MeOH:water | 3:6:3 | A |
| 35 | HCOOH:MeOH:water |  | A |

AcOH = Acetic acid

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 may be used for guidance. All references mentioned herein are incorporated in their entirety.

What is claimed is:

1. Crystalline ziprasidone HCl having structure

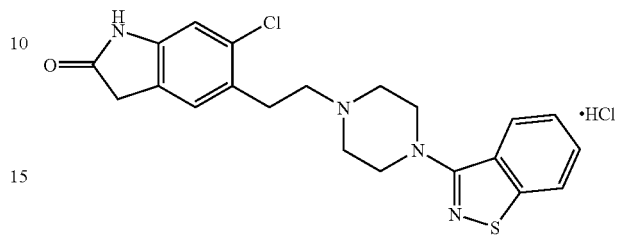

characterized by data selected from the group consisting of a powder XRD pattern with peaks at 10.9, 17.4 and 19.1±0.2 degrees 2 theta and an FTIR spectrum with peaks at about 3400, 3344, 3172, 2949, 970, 940, 872 and 843 cm$^{-1}$.

2. The crystalline ziprasidone HCl of claim 1 characterized by a powder XRD pattern with peaks at 10.9, 17.4 and 19.1±0.2 degrees 2 theta.

3. The crystalline ziprasidone HCl of claim 2 further characterized by a powder XRD pattern with peaks at 25.0 and 26.0±0.2 degrees 2 theta.

4. The crystalline ziprasidone HCl of claim 2 further characterized by a powder XRD pattern with peaks at 13.9, 20.6, 21.3, 21.8 and 23.0±0.2 degrees 2 theta.

5. The crystalline ziprasidone HCl of claim 4 characterized by powder XRD pattern substantially as depicted in FIG. 1.

6. The crystalline ziprasidone HCl of claim 1 characterized by an FTIR spectrum with peaks at 3400, 3344, 3172, 2949, 970, 940, 872 and 843 cm$^{-1}$.

7. The crystalline ziprasidone HCl of claim 6 characterized by an FTIR spectrum substantially as depicted in FIG. 4.

8. The crystalline ziprasidone HCl of claim 1 containing less than about 5% of other polymorphic forms of ziprasidone HCl by weight.

9. The crystalline ziprasidone HCl of claim 1, wherein the crystalline ziprasidone HCl contains less than about 5% of Form M by weight.

10. The crystalline ziprasidone HCl of claim 1, having a water content of about 0.5% to about 6.6% by weight.

11. The crystalline ziprasidone HCl of claim 1, characterized by having high crystallinity.

12. The crystalline ziprasidone HCl of claim 11, wherein the crystallinity is as substantially depicted in FIG. 2 or 3.

13. The crystalline ziprasidone HCl of claim 1, characterized by having specific surface area higher than about 4 m$^2$/g as measured by BET.

14. The crystalline ziprasidone HCl of claim 13, characterized by having specific surface area of about 5 to about 20 m$^2$/g.

15. The crystalline ziprasidone HCl of claim 1, of which no more than about 5% transform to Form M upon heating to a temperature of up to about 140° C.

16. Solid crystalline ziprasidone HCl of claim 1 having a water content of about 4.6% to about 6.6% by weight.

17. The crystalline ziprasidone HCl of claim 1, of which no more than about 5% transform to Form M upon storage at 0% relative humidity for at least 20 days.

18. The crystalline ziprasidone HCl of any one of claims 1 or 17, of which no more than about 5% transform to Form M upon storage at a temperature of about 25 to 55° C. for at least 3 months.

19. The crystalline ziprasidone HCl of claim 18, wherein no more than about 5% transform to Form M upon storage at a temperature of from about 25 to 55° C. for at least 6 months.

20. The crystalline ziprasidone HCl of claim 16, having specific surface area higher than about 4 m$^2$/g.

21. The crystalline ziprasidone HCl of claim 20, characterized by having specific surface area of about 5 to about 20 m$^2$/g.

22. A pharmaceutical composition comprising crystalline ziprasidone HCl of claim 16 and a pharmaceutically acceptable excipient.

23. A pharmaceutical composition comprising an effective amount of the crystalline ziprasidone HCl having a powder XRD pattern with peaks at about 10.9, 17.4 and 19.1, 25.0, 26.0±0.2 degrees 2 theta.

24. Solid crystalline ziprasidone HCl of claim 1 having specific surface area higher than about 4 m$^2$/g.

25. The crystalline ziprasidone HCl of claim 24, characterized by having specific surface area of about 5 to about 20 m$^2$/g.

26. A pharmaceutical composition of ziprasidone HCl prepared by a process comprising:
    a) providing crystalline ziprasidone HCl of claim 24;
    b) admixing the ziprasidone HCl with at least a single pharmaceutically acceptable excipient.

* * * * *